(12) United States Patent
Lynch, Jr. et al.

(10) Patent No.: US 6,380,195 B1
(45) Date of Patent: *Apr. 30, 2002

(54) METHOD OF TREATING HEART FAILURE WITH ENDOTHELIN ANTAGONISTS

(75) Inventors: Joseph J. Lynch, Jr.; You-Tang Shen, both of Lansdale, PA (US)

(73) Assignee: Banyu Pharmaceutical Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 11 days.

(21) Appl. No.: 09/507,666

(22) Filed: Feb. 22, 2000

Related U.S. Application Data

(63) Continuation of application No. 09/132,514, filed on Aug. 11, 1998, now Pat. No. 6,087,360, which is a continuation of application No. 08/824,848, filed on Mar. 26, 1997, now Pat. No. 5,834,483.
(60) Provisional application No. 60/014,882, filed on Apr. 4, 1996.

(51) Int. Cl.$^7$ .................. A61K 31/495; A61K 31/505; A61K 31/44
(52) U.S. Cl. ............ 514/248; 514/249; 514/258; 514/299
(58) Field of Search .................. 514/248, 249, 514/299, 258

(56) References Cited

U.S. PATENT DOCUMENTS 5,834,483 A    11/1998   Lynch, Jr. et al.
6,087,360 A  *  7/2000   Lynch, Jr. et al. .......... 514/248

* cited by examiner

*Primary Examiner*—Raymond Henley, III
(74) *Attorney, Agent, or Firm*—Oblon, Spivak, McClelland, Maier & Neustadt, P.C.

(57) ABSTRACT

A composition for preventing and/or treating heart failure and ventricular dysfunction in a warm blooded animal comprising a therapeutically effective amount of an endothelin antagonist of the formula:

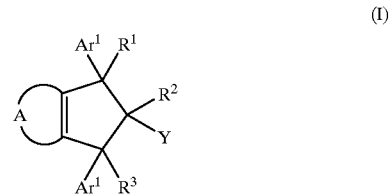

is disclosed

18 Claims, 8 Drawing Sheets

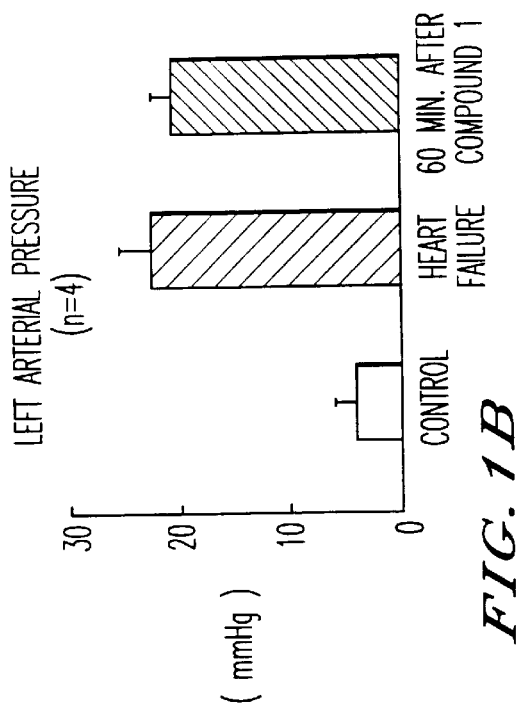
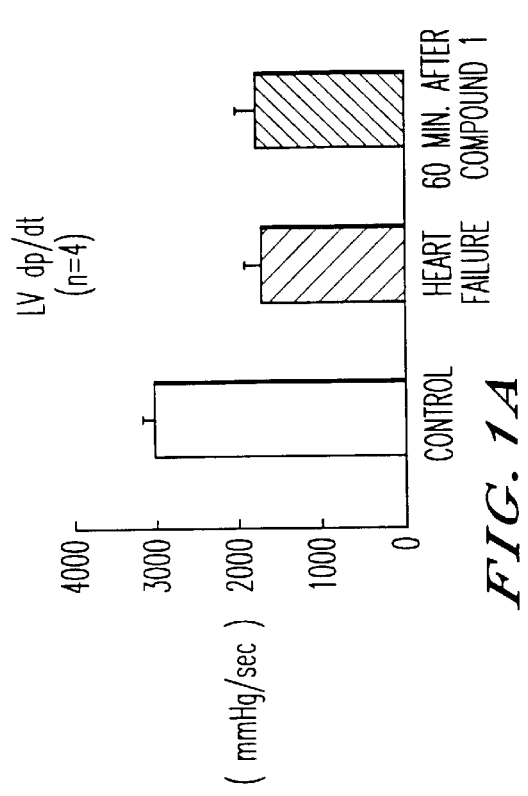
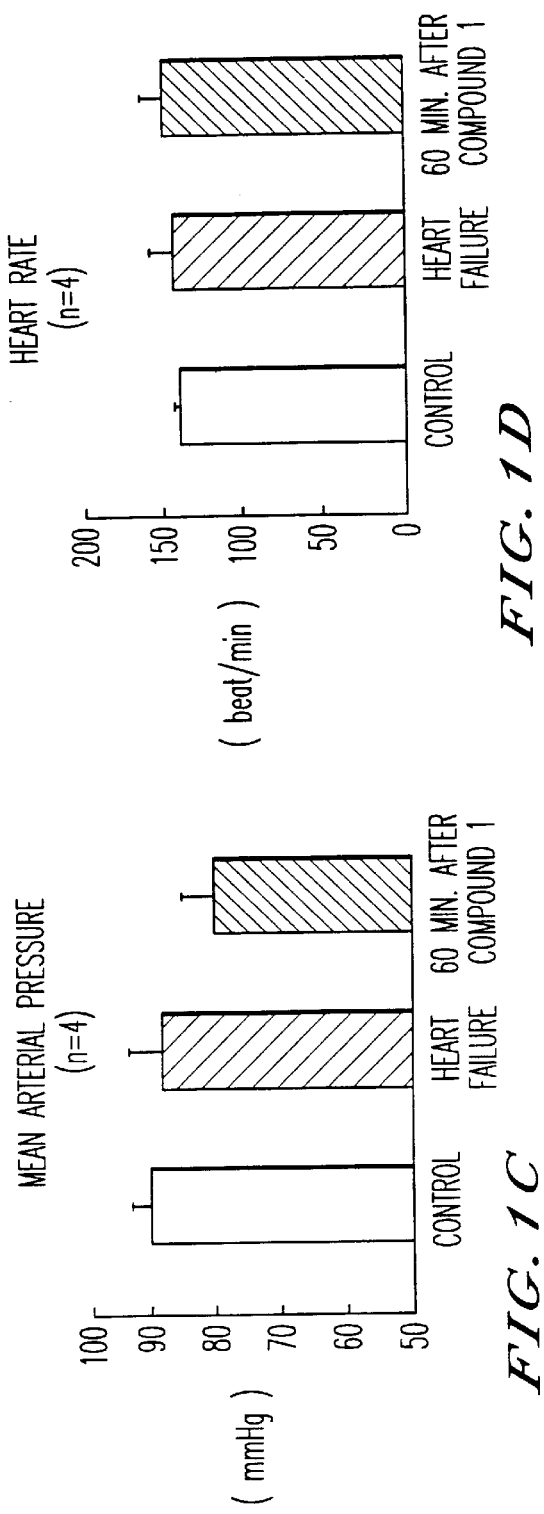

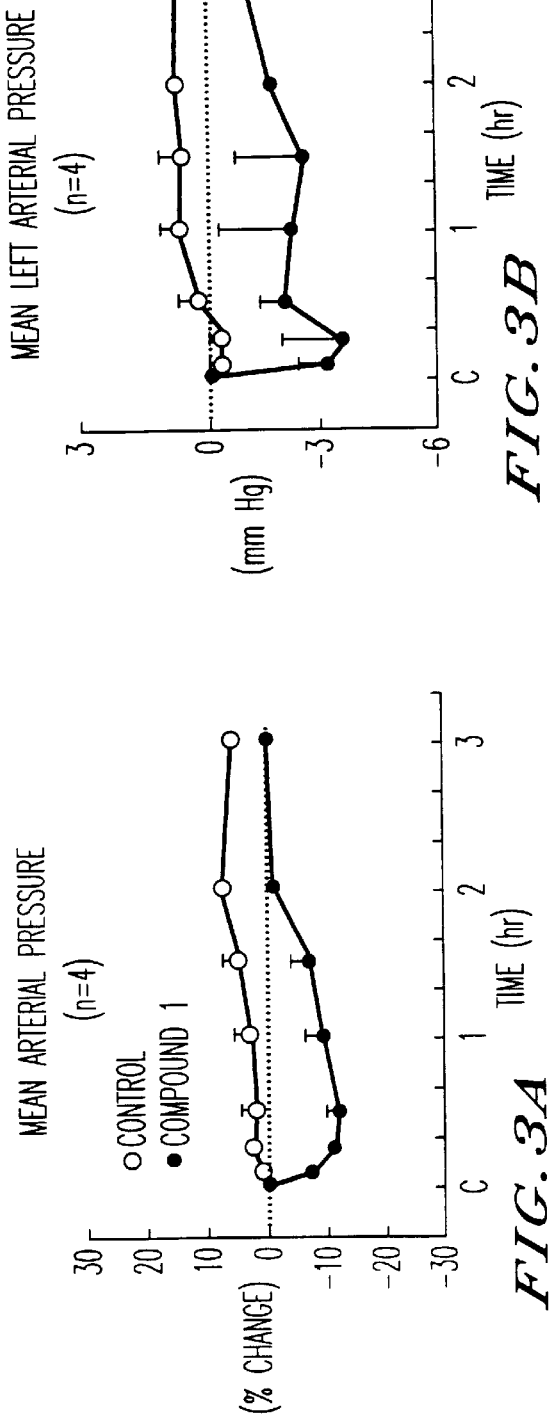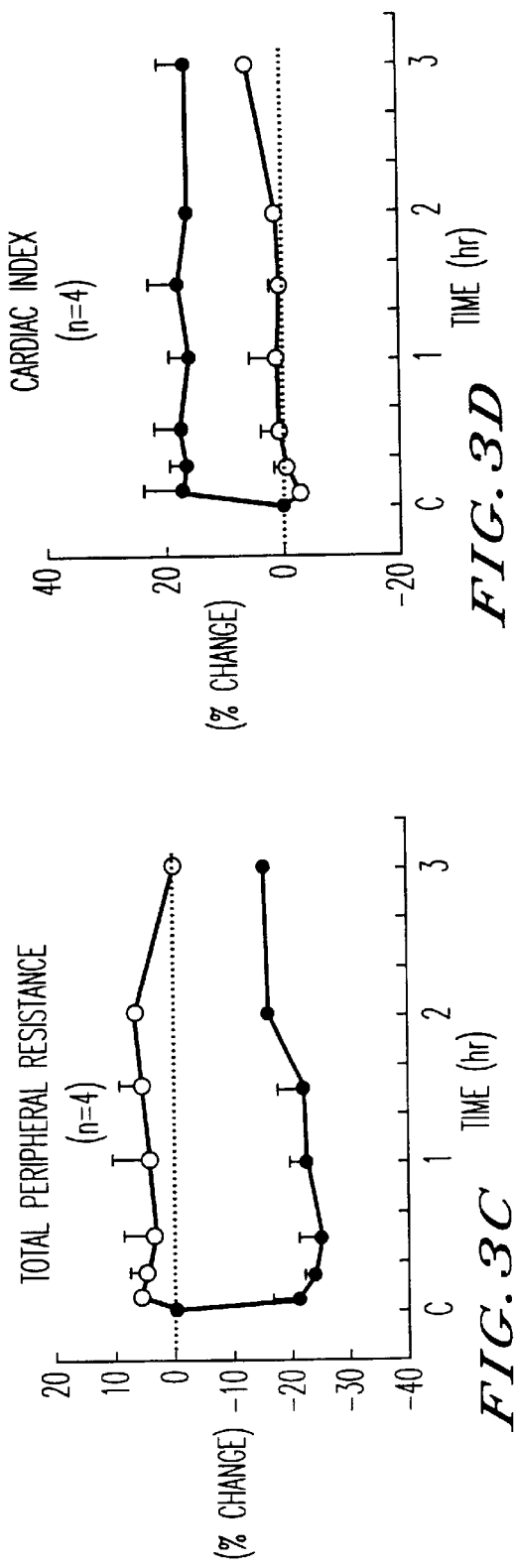

METHOD OF TREATING HEART FAILURE WITH ENDOTHELIN ANTAGONISTS

This application is a continuation of application Ser. No. 09/132,514, filed Aug. 11, 1998, now U.S. Pat. No. 6,087, 360, which is a continuation of application Ser. No. 08/824, 848, filed Mar. 26, 1997, now U.S. Pat. No. 5,834,483, issued Nov. 10, 1998, which filed as provisional application No. 60/014,882, filed Apr. 4, 1996.

FIELD OF THE INVENTION

The present invention is concerned with prevention and/or treatment of heart failure with compounds that are endothelin antagonists.

BACKGROUND OF THE INVENTION

Endothelin is a 21-amino acid peptide produced by endothelial cells. The peptide is secreted not only by vascular endothelial cells but also by tracheal epithelial cells or from kidney cells. Endothelin (ET-1) has a potent vasoconstrictor effect. The vasoconstricting effect is caused by the binding of endothelin to its receptor on the vascular smooth muscle cells.[1-3]

Endothelin-1 (ET-1) is one of three recently identified potent vasoconstricting peptides which also includes endothelin-2 (ET-2) and endothelin-3 (ET-3) whose sequences differ from ET-1 by two and six amino acids, respectively.[4]

Increased levels of endothelin are found in the blood of patients with essential hypertension, acute myocardial infarction, pulmonary hypertension, Raynaud's disease or atherosclerosis or in the washing fluids of the respiratory tract of patients with asthma compared to normal levels.[5-8]

An experimental model of cerebral vasospasm and a second model of acute renal failure have led to the conclusion that endothelin is one of the mediators causing cerebral vasospasm following a subarachnoid hemorrhage, and renal failure.[9-10]

Endothelin was also found to control the release of many physiological substances such as renin, atrial natriuretic peptide, endothelium-derived relaxing factor (EDRF), thromboxane $A_2$,[14] prostacyclin, norepinephrine, angiotensin II and substance P.[11-16] Further, endothelin causes contraction of the smooth muscle of the gastrointestinal tract and the uterine smooth muscle.[17-19] Endothelin has also been shown to promote the growth of rat vascular smooth muscle cells which would suggest a possible relevance to arterial hypertrophy.[20]

Endothelin receptors are present in high concentration in the peripheral tissues and also in the central nervous system, and cerebral administration of endothelin has been shown to induce behavioral changes in animals, suggesting that endothelin may play an important role in controlling neural functions.[21]

Endotoxin has been shown to promote the release of endothelin. This finding has suggested that endothelin is an important mediator for endotoxin-induced diseases.[22-23]

A study has shown that cyclosporin added to a renal cell culture, increased endothelin secretion.[24] Another study has shown that administration of cyclosporin to rats, led to a decrease in the glomerular filtration rate and an increase in the blood pressure, in association with a remarkable increase in the circulating endothelin level. This cyclosporin-induced renal failure can be suppressed by the administration of anti-endothelin antibody.[25] These studies suggest that endothelin is significantly involved in the pathogenesis of cyclosporin-induced renal disease.

A recent study in patients with congestive heart failure demonstrated a good correlation between the elevated levels of endothelin in the plasma and the severity of the disease.[26]

Endothelin is an endogenous substance which directly or indirectly (through the controlled release of various other endogenous substances) induces sustained contraction of vascular or non-vascular smooth muscles. Its excess production or excess secretion is believed to be one of the factors responsible for hypertension, pulmonary hypertension, Raynaud's disease, bronchial asthma, acute renal failure, myocardial infarction, angina pectoris, arteriosclerosis, cerebral vasospasm and cerebral infarction. See A. M. Doherty, *Endothelin: A New Challenge*, J. Med. Chem., 35, 1493–1508 (1992).

Substances which specifically inhibit the binding of endothelin to its receptor are believed to block the physiological effects of endothelin and are useful in treating patients with endothelin related disorders.

The novel compounds of the present invention are useful as a non-peptidic endothelin antagonists, and have not been disclosed in any issued patents or published patent applications. Among the published patent applications disclosing linear and cyclic peptidic compounds as endothelin antagonists are the following: Fujisawa in European Patent Application EP-457,195 and Patent Cooperation Treaty (PCT) International Application No. WO 93/10144, Banyu in EP-436,189 and 460,679, Immunopharmaceutics Inc. in WO 93/225580, Warner Lambert Co. WO 92/20706 and Takeda Chemical Ind. in EP-528,312, EP-543,425, EP-547, 317 and WO 91/13089.

Fujisawa has also disclosed two nonpeptidic endothelin antagonist compounds: anthraquinone derivatives produced by a fermentation process using Streptomyces sp. No. 89009 in EP-405,421 and U.S. Pat. No. 5,187,195; and a 4-phenoxyphenol derivative produced by a fermentation process using *Penicillium citreonigrum* F-12880 in a UK Patent Application GB 2259450. Shionogi and Co. has also disclosed nonpeptidic endothelin antagonist triterpene compounds which were produced by a fermentation process using *Myrica cerifera* in WO 92/12991.

Among the non-peptidic endothelin antagonist compounds which are known in the patent literate are: 1) a series of substituted (1,4-quinolinoxy)methylbiphenylcarboxylic acids disclosed by Roussel-Uclaf in EP-498,723; 2) a series of of N-(4-pyrimidinyl)benzenesulfonamides with different substitution patterns from Hoffmann-La Roche published in EP-510,526, EP-526,708 and EP-601,386; 3) a series of naphthalenesulfonamides and benzenesulfonamides disclosed by E. R. Squibb & Sons in EP-558,258 and EP-569, 193, respectively; 4) a series of compounds represented by 3-(3-indolylmethyl)-1,4-diaza-2,5-dioxobicyclo[4.3.0] nonane-9-carboxylic acid from ImmunoPharmaceutics Inc. in WO 93/23404; 5) a series of fused [1,2,4]thiadiazoles substituted with an iminosulfonyl substituent from Takeda Chemical Ind. has been disclosed in EP-562,599; and 6) a series of indane and indene derivatives from SmithKline Beecham Corp. disclosed in WO 93/08779; and a series of related phenylalkyl derivatives from SmithKline Beecham disclosed in WO 94/02474.

REFERENCES

1 Nature, 332, 411–415 (1988).
2 FEBS Letters, 231, 440–444 (1988).
3 Biochem. Biophys. Res. Commun. 154, 868–875 (1988).

4 TiPS, 13, 103–108, March 1992.
5 Japan J. Hypertension 12, 79 (1989).
6 J. Vascular Medicine Biology, 2, 207 (1990).
7 J. Am. Med. Association, 264, 2868 (1990).
8 The Lancet, ii, 207 (1990) and The Lancet, ii, 747–748 (1989).
9 Japan. Soc. Cereb. Blood Flow & Metabol. 1, 73 (1989).
10 J. Clin. Invest., 83, 1762–1767 (1989).
11 Biochem. Biophys. Res. Comm. 157, 1164–1168 (1988).
12 Biochem. Biophys. Res. Comm. 155, 167–172 (1989).
13 Proc. Natl. Acad. Sci. USA, 85, 9797–9800 (1989).
14 J. Cardiovasc. Pharmacol., 13, 589–592 (1989).
15 Japan. J. Hypertension 12, 76 (1989).
16 Neuroscience Letters, 102, 179–184 (1989).
17 FEBS Letters, 247, 337–340 (1989).
18 Eur. J. Pharmacol. 154, 227–228 (1988).
19 Biochem. Biophys. Res. Commun., 159, 317–323 (1989).
20 Atherosclerosis, 78, 225–228 (1989).
21 Neuroscience Letters, 97, 276–279 (1989).
22 Biochem. Biophys. Res. Commun. 161, 1220–1227 (1989).
23 Acta. Physiol. Scand., 137, 317–318 (1989).
24 Eur. J. Pharmacol., 180, 191–192 (1990).
25 Kidney Int. 37, 1487–1491 (1990).
26 Mayo Clinic Proc., 67, 719–724 (1992).

SUMMARY OF THE INVENTION

The present invention is concerned with the prevention and/or treatment of heat failure and ventricular dysfunction with endothelin antagonists.

BRIEF DESCRIPTION OF THE FIGURES

FIG. 1.

Figure 2A:
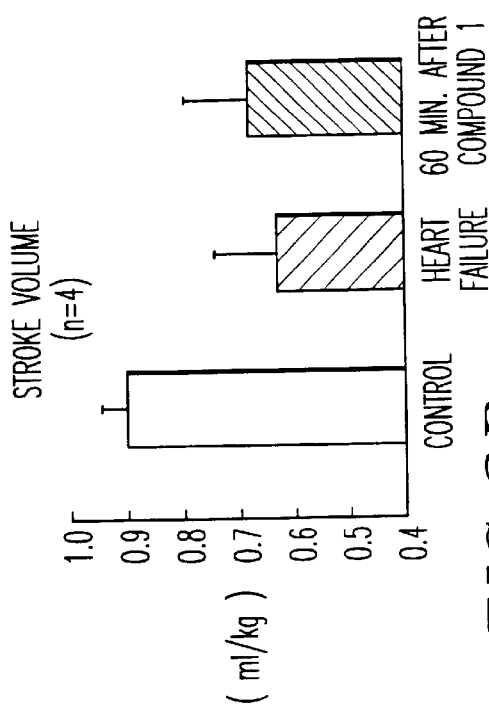
Figure 2B:
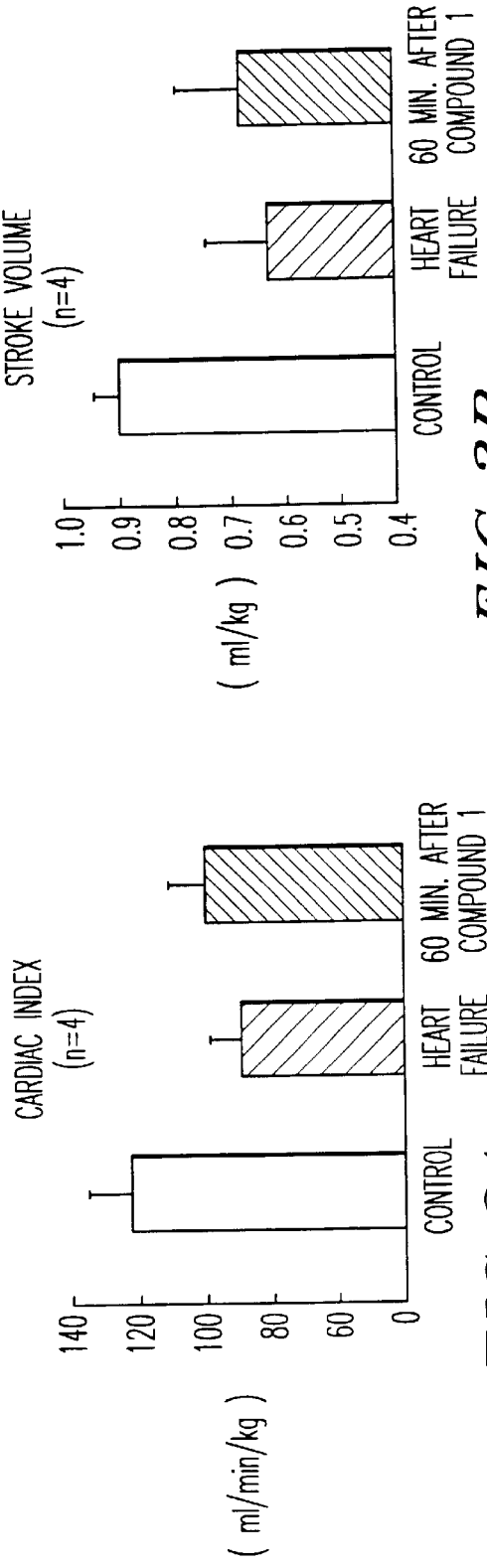
Figure 2C:
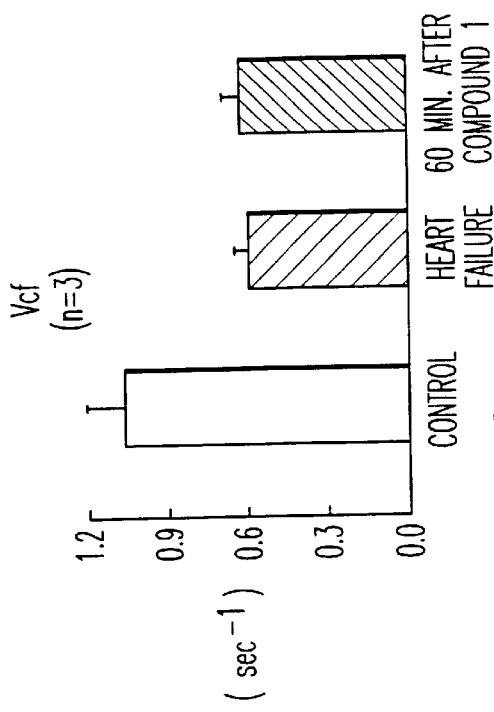
Figure 2D:
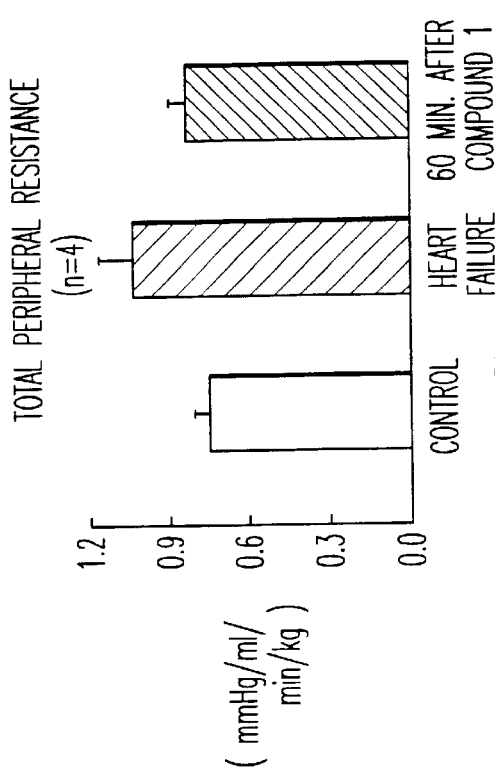
Figure 4A:
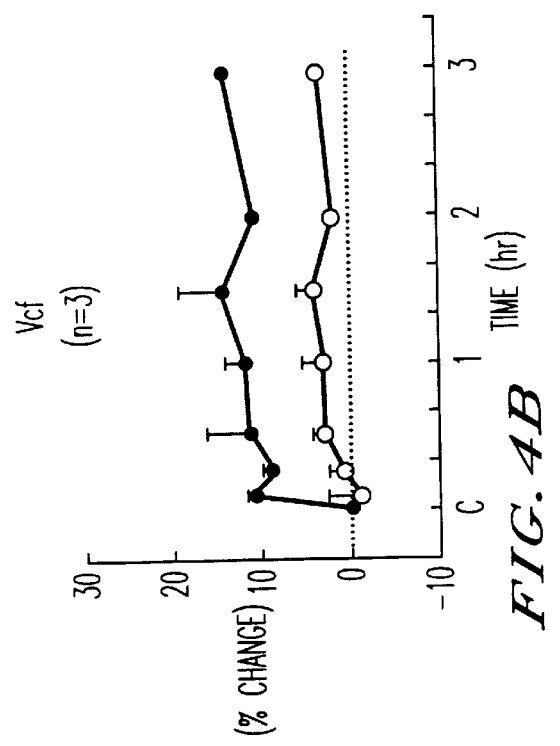
Figure 4C:
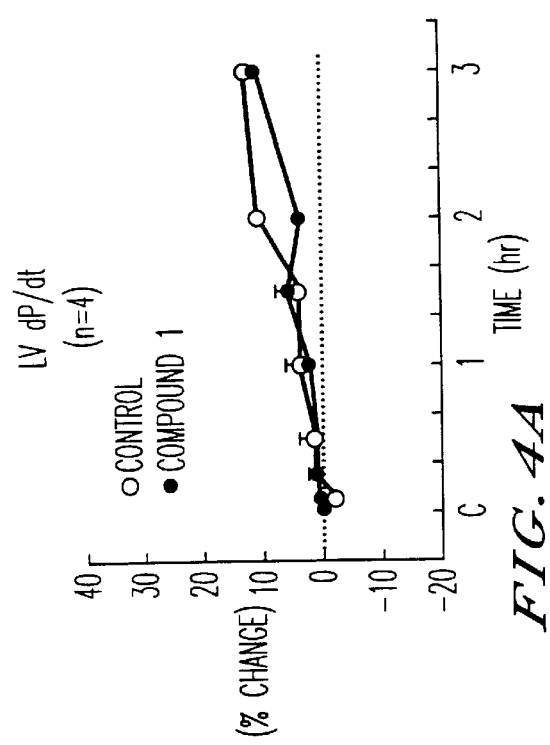
Figure 4B:
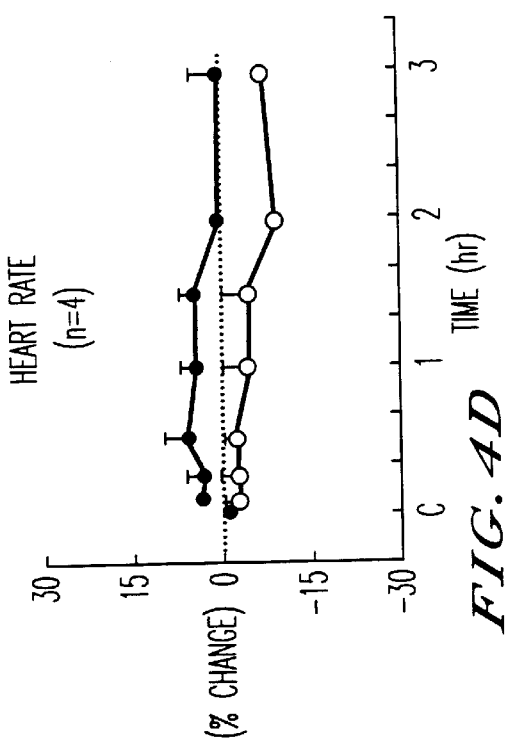
Figure 4D:
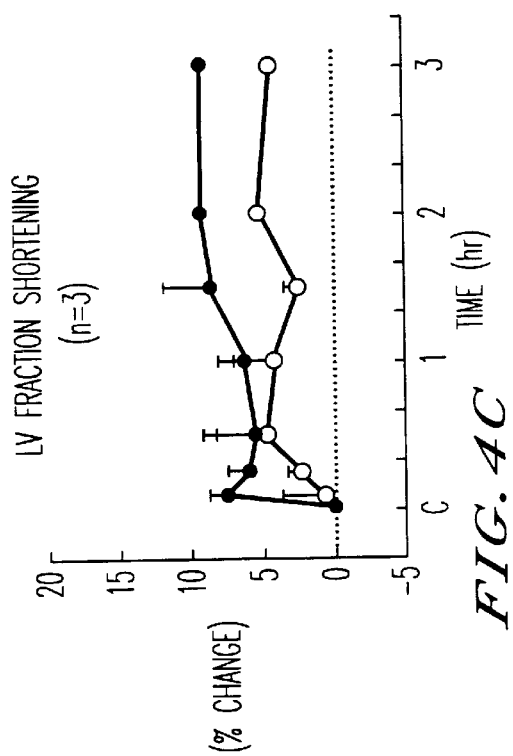

Measurements of LV dP/dt, mean left atrial pressure, mean arterial pressure and heart rate made in the same conscious pigs before and after development of heart failure, and 60 min after injection of Compound 1 (0.5 mg/kg, i.v.) during the heart failure stage. Data are mean±SE and the number of animals studied is in parenthesis.

FIG. 2.

Measurements of cardiac index, stroke volume, total peripheral resistance and LV velocity of circumferential fibre shortening (Vcf) made in the same conscious pigs before and after development of heart failure, and 60 min after injection of Compound 1 (0.5 mg/kg, i.v.) during the heart failure stage. Data are mean±SE and the number of animals studied is in parenthesis.

FIG. 3.

Effects of Compound 1 (0.5 mg/kg, i.v.) on mean arterial pressure, mean left atrial pressure, cardiac index and total peripheral resistance in conscious pigs after development of heart failure. Values are expressed as the percent changes from baseline levels, except mean left atrial pressure which is change from baseline value in mmHg. Data are mean±SE and the number of animals studied is in parenthesis.

FIG. 4.

Effects of Compound 1 (0.5 mg/kg, i.v.) on LV dP/dt, LV velocity of circumferential fibre shortening (Vcf), LV fractional shortening and heart rate in conscious pigs after development of heart failure. Values are expressed ah the percent changes from baseline levels. Data are mean±SE and the number of animals studied is in parenthesis.

FIG. 5.

Effects of Compound 1 (0.5 mg/kg, I.V.) and Compound 2 (1 mg/kg and 4 mg/kg, i.v.) on total peripheral resistance in conscious pigs after development of heart failure. Values are expressed as the percent change.

from baseline levels. Data are mean±SE and the number of animals studied is in parenthesis.

FIG. 6.

Comparison of the mean arterial pressure (MAP), LV dP/dt, cardiac output (CO) and total peripheral resistance (TPR) responses at 60 min after injection of Compound 1 (0.5 mg/kg, i.v.) or Compound 2 (1 mg/kg and 4 mg/kg, i.v.) in conscious pigs after development of heart failure. Values are expressed as the percent changes from baseline levels. Data are mean±SE and the number of animals studied is in parenthesis.

FIG. 7.

Effects of endothelin-1 (ET-1, 0.1 to 0.5 μg/kg, i.v.) on mean arterial pressure, mean left arterial pressure, total peripheral resistance and heart rate in conscious pigs after development of heart failure with and without Compound 1 (0.5 mg/kg, i.v.). Values are expressed as the percent changes from baseline levels, except mean left atrial pressure which is change from baseline value in mmHg. Data are mean±SE and the number of animals studied is in parenthesis.

FIG. 8.

Chronically instrumented heart failure model.

DESCRIPTION OF THE INVENTION

The present invention involves a method of preventing and/or treating heart failure and ventricular dysfunction in a warm blooded animal which comprises administering to the warm blooded animal in need of such treatment a therapeutically effective amount of an endothelin antagonist of the formula:

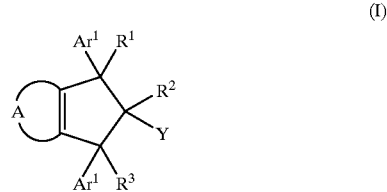

(I)

or a pharmaceutically acceptable salt thereof wherein:
each of $Ar^1$ and $Ar^2$ is independently a phenyl group, a thienyl group, a pyridyl group, an indolyl group, a benzofuranyl group or a dihydrobenzofuranyl group wherein an optional hydrogen atom(s) on the aromatic ring may be replaced with 1 to 4 groups selected from the group consisting of a halogen atom, a hydroxyl group, an amino group, a carboxyl group, a $C_1$–$C_6$ alkoxycarbonyl group, a mono- or di-$C_1$–$C_6$ alkylaminocarbonyl group, a carbamoyl group, a tetrazol-5-yl group, a methylenedioxy group, a $C_1$–$C_6$ alkoxy group, a $C_2$–$C_6$ alkenyloxy group, a mono- or di-$C_1$–$C_6$ alkylamino group, a $C_1$–$C_6$ alkyl group, a $C_2$–$C_6$ alkenyl group and a $C_2$–$C_6$ alkynyl group (provided that the $C_1$–$C_6$ alkoxy group, $C_2$–$C_6$ alkenyloxy group, mono- or di-$C_1$–$C_6$ alkylamino group, $C_1$–$C_6$ alkyl group, $C_2$–$C_6$ alkenyl group and $C_2$–$C_6$ alkynyl group may be substituted by 1 to 3 groups selected from the group consisting of a phenyl group, a pyridyl group, an imidazolyl group, a hydroxyl group, a $C_1$–$C_6$ alkoxy group, an amino group, a mono- or di-$C_1$–$C_6$ alkylamino group, a hydroxy $C_1$–$C_6$ alkylcarbonyl group, a $C_1$–$C_6$ acyloxy $C_1$–$C_6$ alkylcarbonyl group, a carboxy $C_1$–$C_6$ alkoxycarbonyl group, a carboxy $C_1$–$C_6$ alkoxycarbonyl $C_1$–$C_6$ alkoxycarbonyl group, a $C_1$–$C_6$ alkoxycarbonyl group, a mono- or di-$C_1$–$C_6$ alkylaminocarbonyl group, a carbamoyl group, a $C_1$–$C_6$ alkylsulfonylaminocarbonyl group, a tetrazol-5-ylaminocarbonyl group, a carboxyl group, $SO_3H$, $PO_3H_2$, a tetrazol-5-yl group, a 2-oxo-3H-1,2,3,5-oxathiadiazol-4-yl group and a 5-oxo-4H-1,2,4-oxadiazol-3-yl group (provided that when a hydroxyl group and a carboxyl group are selected as substituents, they may together form a lactone ring));

each of $R^1$, $R^2$ and $R^3$ is independently a hydrogen atom, a hydroxyl group or a $C_1$–$C_6$ alkyl group, or $R^1$ and $R^2$, or $R^2$ and $R^3$ together form a single bond;

Y is a group of —CO—$R^4$ (wherein $R^4$ is a hydroxyl group, an amino group, a $C_1$–$C_6$ alkoxy group, a mono- or di-$C_1$–$C_6$ alkylamino group, a $C_1$–$C_6$ alkylsulfonylamino group, or an arylsulfonylamino group or aryl $C_1$–$C_6$ alkylsulfonylamino group wherein an optional hydrogen atom(s) on the aryl ring may be replaced with a $C_1$–$C_6$ alkyl group), $SO_3H$, $PO_3H_2$, a tetrazol-5-yl group, a 2-oxo-3H-1,2,3,5-oxathiadiazol-4-yl group or a 5-oxo-4H-1,2,4-oxadiazol-3-yl group; and A is a group which forms together with the adjacent carbon-carbon double bond a 5- or 6-membered heteroaromatic ring including 1 to 4 hetero atoms selected from the group consisting of a nitrogen atom, an oxygen atom and a sulfur atom (provided that optional 1 or 2 hydrogen atoms on the heteroaromatic ring may be replaced with a hydroxyl group, an amino group, a $C_1$–$C_6$ alkoxy group, a $C_1$–$C_6$ alkylthio group, a halogen atom, a cyano group, a nitro group, a mono- or di-$C_1$–$C_6$ alkylamino group which may be substituted by a hydroxyl group at the alkyl moiety, a $C_3$–$C_8$ cycloalkylamino group which may be substituted by a hydroxyl group at the alkyl or alkylene moiety, a $C_3$–$C_8$ cycloalkyl $C_1$–$C_6$ alkylamino group which may be substituted by a hydroxyl group at the alkyl or alkylene moiety, an N-($C_1$–$C_6$ alkyl)-N-($C_3$–$C_8$ cycloalkyl) amino group which may be substituted by a hydroxyl group at the alkyl or alkylene moiety, an N-($C_1$–$C_6$ alkyl)-N-(aroyl)amino group which may be substituted by a hydroxyl group at the alkyl moiety, a $C_4$–$C_7$ cyclic imino group which may be substituted by a hydroxyl group at the alkylene moiety, a carboxyl group, a $C_1$–$C_6$ alkoxycarbonyl group, a formyl group, a $C_2$–$C_6$ alkanoyl group, an aroyl group, or a $C_1$–$C_6$ alkyl group, $C_3$–$C_8$ cycloalkyl group, $C_3$–$C_8$ cycloalkyl $C_1$–$C_6$ alkyl group, $C_2$–$C_6$ alkenyl group or $C_2$–$C_6$ alkynyl group which may be substituted by 1 to 3 substituents selected from the group consisting of a hydroxyl group, an amino group, a $C_1$–$C_6$ alkoxy group and a mono- or di-$C_1$–$C_6$ alkylamino group, and when the heteroaromatic ring includes one or more nitrogen atoms, the nitrogen atom(s) may be oxidized to form an N-oxide group) or a pharmaceutically acceptable salt thereof.

Now, this invention will be described in more detail with reference to specific examples for the various symbols used in the formula (I).

Each of $AR^1$ and $Ar^2$ is independently a phenyl group, a thienyl group, a pyridyl group, an indolyl group, a benzofuranyl group or a dihydrobenzofuranyl group wherein an optional hydrogen atom(s) on the aromatic ring may be replaced with 1 to 4 groups selected from the group consisting of a halogen atom, a hydroxyl group, an amino group, a carboxyl group, a $C_1$–$C_6$ alkoxycarbonyl group, a mono- or di-$C_1$–$C_6$ alkylaminocarbonyl group, a carbamoyl group, a tetrazol-5-yl group, a methylenedioxy group, a $C_1$–$C_6$ alkoxy group, a $C_2$–$C_6$ alkenyloxy group, a mono- or di-$C_1$–$C_6$ alkylamino group, a $C_1$–$C_6$ alkyl group, a $C_2$–$C_6$ alkenyl group and a $C_2$–$C_6$ alkynyl group (provided that the $C_1$–$C_6$ alkoxy group, $C_2$–$C_6$ alkenyloxy group, mono- or di-$C_1$–$C_6$ alkylamino group, $C_1$–$C_6$ alkyl group, $C_2$–$C_6$ alkenyl group and $C_2$–$C_6$ alkynyl group may be substituted by 1 to 3 groups selected from the group consisting of a phenyl group, a pyridyl group, an imidazolyl group, a hydroxyl group, a $C_1$–$C_6$ alkoxy group, an amino group, a mono- or di-$C_1$–$C_6$ alkylamino group, a hydroxy $C_1$–$C_6$ alkylcarbonyl group, a $C_1$–$C_6$ acyloxy $C_1$–$C_6$ alkylcarbonyl group, a carboxy $C_1$–$C_6$ alkoxycarbonyl group, a carboxy $C_1$–$C_6$ alkoxycarbonyl $C_1$–$C_6$ alkoxycarbonyl group, a $C_1$–$C_6$ alkoxycarbonyl group, a mono- or di-$C_1$–$C_6$ alkylaminocarbonyl group, a carbamoyl group, a $C_1$–$C_6$ alkylsulfonylaminocarbonyl group, a tetrazol-5-ylaminocarbonyl group, a carboxyl group, $SO_3H$, $PO_3H_2$, a tetrazol-5-yl group, a 2-oxo-3H-1,2,3,5-oxathiadiazol-4-yl group and a 5-oxo-4H-1,2,4-oxadiazol-3-yl group (provided that when a hydroxyl group and a carboxyl group are selected as substituents, they may together form a lactone ring)).

The halogen atom means a fluorine, chlorine, bromine or iodine atom.

The $C_1$–$C_6$ alkoxycarbonyl group means an alkoxycarbonyl group having a linear or branched $C_1$–$C_6$ alkoxy group such as a methoxycarbonyl, ethoxycarbonyl, propoxycarbonyl, isopropoxycarbonyl, butyloxycarbonyl , isobutyloxycarbonyl, tert-butyloxycarbonyl, pentyloxycarbonyl, isopentyloxycarbonyl or hexyloxycarbonyl group.

The mono- or di-$C_1$–$C_6$ alkylaminocarbonyl group means an alkylaminocarbonyl group having 1 or 2 linear or branched $C_1$–$C_6$ alkyl groups at the nitrogen atom such as a methylaminocarbonyl, ethylaminocarbonyl, propylaminocarbonyl, isopropylaminocarbonyl, buylaminocarbonyl, isobutylaminocarbonyl, tert-buylaminocarbonyl, pentylaminocarbonyl, isopentylaminocarbonyl, hexylaminocarbonyl, dimethylaminocarbonyl group, ethylmethylaminocarbonyl group, diethylaminocarbonyl, isopropylmethylaminocarbonyl, dipropylaminocarbonyl, ethylisopropylaminocarbonyl, diisopropylaminocarbonyl, dibutylaminocarbonyl, diisobutylaminocarbonyl, di-tert-butylaminocarbonyl, dipentylaminocarbonyl, ethylpentylaminocarbonyl, diisopentylaminocarbonyl or ethylhexylaminocarbonyl group.

The $C_1$–$C_6$ alkoxy group means a linear or branched alkoxy group having 1 to 6 carbon atoms such as a methoxy, ethoxy, propoxy, isopropoxy, butoxy, isobutoxy, sec-butoxy, tert-butoxy, pentyloxy or hexyloxy group.

The $C_2$–$C_6$ alkenyloxy group means an alkenyloxy is group having a linear or branched $C_2$–$C_6$ alkenyl group such as a vinyloxy, allyloxy, 1-propenyloxy, isopropenyloxy, 2-butenyloxy, 3-butenyloxy, 2-pentenyloxy, 3-methyl-3-butenyloxy or 2-hexenyloxy group.

The mono- or di-$C_1$–$C_6$ alkylamino group means an alkylamino group having 1 or 2 linear or branched $C_1$–$C_6$ alkyl groups at the nitrogen atom such as a methylamino, ethylamino, propylamino, isopropylamino, butylamino, isobutylamino, tert-butylamino, pentylamino, isopentylamino, hexylamino, dimethylamino, ethylmethylamino, diethylamino, dipropylamino, propylmethylamino, ethylpropylamino, diisopropylamino, diisobutylamino, ethylisobutylamino, di-tert-butylamino, dipentylamino, diisopentylamino, isopentylmethylamino or dihexylamino group, The $C_1$–$C_6$ alkyl group means a linear or branched alkyl group having 1 to 6 carbon atoms such as a methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl or 1-ethyl-1-methylpropyl group.

The $C_2$–$C_6$ alkenyl group means a linear or branched alkenyl group having 2 to 6 carbon atoms such as is a vinyl, allyl, 2-propenyl, isopropenyl, 3-butenyl, 2-butenyl, 1-butenyl, 1-methyl-2-propenyl, 1-methyl-1-propenyl, 1-ethyl-1-ethenyl, 2-methyl-2-propenyl, 2-methyl-1-propenyl or 4-pentenyl group.

The $C_2$–$C_6$ alkynyl group means a linear or branched alkynyl group having 2 to 6 carbon atoms such as an ethynyl, 1-propynyl, 2-propynyl, 1-butynyl, 2-butynyl, 3-butynyl, 1-methyl-2-propynyl or 1-pentynyl group.

The hydroxy $C_1$–$C_6$ alkylcarbonyl group means a linear or branched hydroxyalkylcarbonyl group having 2 to 7 carbon atoms such as a hydroxymethylcarbonyl, 1-hydroxyethylcarbonyl, 1-hydroxypropylcarbonyl, 1-hydroxybutylcarbonyl, 1-hydroxypentylcarbonyl, 1-hydroxyhexylcarbonyl, 2-hydroxyethylcarbonyl, 3-hydroxypropylcarbonyl, 2-hydroxybutylcarbonyl, 4-hydroxypentylcarbonyl, 3-hydroxyhexylcarbonyl or 2-hydroxy-2-methylpropylcarbonyl group.

The $C_1$–$C_6$ acyloxy $C_1$–$C_6$ alkylcarbonyl group means an acyloxy $C_1$–$C_6$ alkylcarbonyl group having a aliphatic or aromatic acyloxy group such as an acetyloxymethylcarbonyl, 1-acetyloxyethylcarbonyl, 2-acetyloxyethylcarbonyl, 1-acetyloxypropylcarbonyl, 1-acetyloxybutylcarbonyl, 1-acetyloxypentylcarbonyl, 1-acetyloxyhexylcarbonyl, 2-acetyloxypropylcarbonyl, propionyloxymethylcarbonyl, 1-propionyloxyethylcarbonyl, butylyloxymethylcarbonyl, pentanoyloxymethylcarbonyl, hexanoyloxymethylcarbonyl, benzoyloxymethylcarbonyl, 1-benzoyloxyethylcarbonyl, 2-benzoyloxyethylcarbonyl, thienylcarbonyloxymethylcarbonyl, furfuryloxymethylcarbonyl, pyridylcarbonyloxymethylcarbonyl or imidazolylcarbonyloxymethylcarbonyl group.

The carboxy $C_1$–$C_6$ alkoxycarbonyl group means a linear or branched carboxy $C_1$–$C_6$ alkoxycarbonyl group having 3 to 10 carbon atoms such as a carboxymethoxycarbonyl, 1-carboxyethoxycarbonyl, 1-carboxypropoxycarbonyl, 1-carboxybutoxycarbonyl, 2-carboxyethoxycarbonyl, 2-carboxybutoxycarbonyl, 2-carboxypentoxycarbonyl, 3-carboxypropoxycarbonyl, 3-carboxybutoxycarbonyl, 4-carboxypentoxycarbonyl, 3-carboxyhexyloxycarbonyl or 2-carboxy-2-methylpropyloxycarbonyl group.

The carboxy $C_1$–$C_6$ alkoxycarbonyl $C_1$–$C_6$ alkoxycarbonyl group means a linear or branched carboxy $C_1$–$C_6$ alkoxycarbonyl $C_1$–$C_6$ alkoxycarbonyl group having 3 to 16 carbon atoms such as a carboxymethoxycarbonylmethoxycarbonyl, 1-carboxyethoxycarbonylmethoxycarbonyl, 1-carboxypropoxycarbonylmethoxycarbonyl, 1-carboxybuoxycarbonylmethoxycarbonyl, 2-carboxyethoxycarbonylmethoxycarbonyl 2-carboxybutoxycarbonylethoxycarbonyl, 2-carboxypentoxycarbonylethoxycarbonyl, 3-carboxypropoxycarbonylethoxycarbonyl, 3-carboxybutoxycarbonylethoxycarbonyl, 4-carboxypentoxycarbonylethoxycarbonyl, 3-carboxyhexyloxycarbonylmethoxycarbonyl or 2-carboxy-2-methylpropyloxycarbonylmethoxycarbonyl group.

The $C_1$–$C_6$ alkylsulfonylaminocarbonyl group means an alkylsulfonylaminocarbonyl group having a linear or branched $C_1$–$C_6$ alkyl group such as a methylsulfonylaminocarbonyl, ethylsulfonylaminocarbonyl, propylsulfonylaminocarbonyl, isopropylsulfonylaminocarbonyl, butylsulfonylaminocarbonyl, isobutylsulfonylaminocarbonyl, tert-butylsulfonylaminocarbonyl, pentylsulfonylaminocarbonyl, isopentylsulfonylaminocarbonyl or hexylsulfonylaminocarbonyl group.

Preferred compounds useful in the present invention are those where $Ar^1$ and $Ar^2$ are independently a phenyl group, a thienyl group or a dihydrobenzofuranyl group wherein an optional hydrogen atom(s) on the aromatic ring may be replaced with 1 to 4 groups selected from the group consisting of a halogen atom, a hydroxyl group, an amino group, a methylenedioxy group, a $C_1$–$C_6$ alkoxy group, a $C_2$–$C_6$ alkenyloxy group, a mono- or di-$C_1$–$C_6$ alkylamino group, a $C_1$–$C_6$ alkyl group, a $C_2$–$C_6$ alkenyl group and a $C_2$–$C_6$ alkynyl group (provided that the said $C_1$–$C_6$ alkoxy group, $C_2$–$C_6$ alkenyloxy group, mono- or di-$C_1$–$C_6$ alkylamino group, $C_1$–$C_6$ alkyl group, $C_2$–$C_6$ alkenyl group and $C_2$–$C_6$ alkynyl group may be substituted by 1 to 3 groups selected from the group consisting of a phenyl group, a pyridyl group, an imidazolyl group, a hydroxyl group, a $C_1$–$C_6$ alkoxy group, an amino group, a mono- or di-$C_1$–$C_6$ alkylamino group, a hydroxy $C_1$–$C_6$ alkylcarbonyl group, a $C_1$–$C_6$ acyloxy $C_1$–$C_6$ alkylcarbonyl group, a carboxy $C_1$–$C_6$ alkoxycarbonyl group, a carboxy $C_1$–$C_6$ alkoxycarbonyl $C_1$–$C_6$ alkoxycarbonyl group, a $C_1$–$C_6$ alkoxycarbonyl group, a mono- or di-$C_1$–$C_6$ alkylaminocarbonyl group, a carbamoyl group, a $C_1$–$C_6$ alkylsulfonylaminocarbonyl group, a tetrazol-5-ylaminocarbonyl group, a carboxyl group, a tetrazol-5-yl group, a 2-oxo-3H-1,2,3,5-oxathiadiazol-4-yl group and a 5-oxo-4H-1,2,4-oxadiazol-3-yl group (provided that when a hydroxyl group and a carboxyl group are selected as the substituents, they may together form a lactone ring)).

Each of $R^1$, $R^2$ and $R^3$ is independently a hydrogen atom, a hydroxyl group or a $C_1$–$C_6$ alkyl group, or $R^1$ and $R^2$, or $R^2$ and $R^3$ together form a single bond.

The $C_1$–$C_6$ alkyl group means a linear or branched alkyl group having 1 to 6 carbon atoms such as a methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl or 1-ethyl-1-methylpropyl group.

When $R^1$ and $R^2$, or $R^2$ and $R^3$ together form a single bond, compounds of the general formula (I) are compounds of the general formula ($I^a$) or ($I^b$).

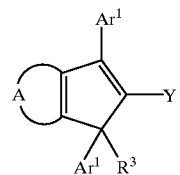

[$I^a$]

-continued

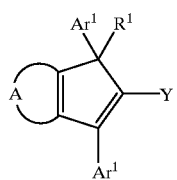

[I$^b$]

Ar$^1$, Ar$^2$, A, R$^1$ and R$^3$ are as defined above.

Y is a group of —CO—R$^4$ (wherein R$^4$ is a hydroxyl group, an amino group, a C$_1$–C$_6$ alkoxy group, a mono- or di-C$_1$–C$_6$ alkylamino group, a C$_1$–C$_6$ alkylsulfonylamino group, or an arylsulfonylamino group or aryl C$_1$–C$_6$ alkylsulfonylamino group wherein an optional hydrogen atom(s) on the aryl ring may be replaced with a C$_1$–C$_6$ alkyl group), SO$_3$H, PO$_3$H$_2$, a tetrazol-5-yl group, a 2-oxo-3H-1,2,3,5-oxathiadiazol-4-yl group or a 5-oxo-4H-1,2,4-oxadiazol-3-yl group.

The C$_1$–C$_6$ alkoxy group means a linear or branched alkoxy group having 1 to 6 carbon atoms such as a methoxy, ethoxy, propoxy, isopropoxy, butoxy, isobutoxy, sec-butoxy, tert-butoxy, pentyloxy or hexyloxy group.

The mono- or di-C$_1$–C$_6$ alkylamino group means an alkylamino group having 1 or 2 linear or branched C$_1$–C$_6$ alkyl groups at the nitrogen atom such as a methylamino, ethylamino, propylamino, isopropylamino, butylamino, isobutylamino, tert-butylamino, pentylamino, isopentylamino, hexylamino, dimethylamino, ethylmethylamino, diethylamino, dipropylamino, propylmethylamino, ethylpropylamino, diisopropylamino, diisobutylamino, ethylisobutylamino, di-tert-butylamino, di pentylamino, diisopentylamino, isopentylmethylamino or dihexylamino group, The C$_1$–C$_6$ alkylsulfonylamino group means an alkylsulfonylamino group having a linear or branched C$_1$–C$_6$ alkyl group such as a methylsulfonylamino, ethylsulfonylamino, propylsulfonylamino, isopropylsulfonylamino, butylsulfonylamino, isobutylsulfonylamino, tert-butylsulfonylamino, pentylsulfonylamino, isopentylsulfonylamino or hexylsulfonylamino group.

The arylsulfonylamino group wherein an optional hydrogen atom(s) on the aryl ring may be replaced with a C$_1$–C$_6$ alkyl group means an arylsulfonylamino group having a C$_6$–C$_{14}$ aromatic hydrocarbon ring or heteroaromatic ring including 1 to 4 hetero atoms selected from the group consisting of an oxygen atom, a nitrogen atom and a sulfur atom, wherein an optional hydrogen atom(s) on the aryl ring may be replaced with a C$_1$–C$_6$ alkyl group, such as a phenylsulfonylamino, naphthylsulfonylamino, thienylsulfonylamino, pyridylsulfonylamino or furylsulfonylamino group, or said groups having a C$_1$–C$_6$ alkyl group on the aromatic ring.

The aryl C$_1$–C$_6$ alkylsulfonylamino group wherein an optional hydrogen atom(s) on the aryl ring may be replaced with a C$_1$–C$_6$ alkyl group means an arylalkylsulfonylamino group having, at the alkyl moiety of the above-defined C$_1$–C$_6$ alkylsulfonylamino group, a C$_6$–C$_{14}$ aromatic hydrocarbon ring or heteroaromatic ring including 1 to 4 hetero atoms selected from the group consisting of an oxygen atom, a nitrogen atom and a sulfur atom, wherein an optional hydrogen atom(s) on the aryl ring may be replaced with a C$_1$–C$_6$ alkyl group, such as a benzylsulfonylamino, phenylethylsulfonylamino, phenylpropylsulfonylamino, 1-methyl-2-phenylethylsulfonylamino, phenylbutylsulfonylamino, phenylpentylsulfonylamino, phenylhexylsulfonylamino, naphthylmethylsulfonylamino, naphthylethylsulfonylamino, naphthylpropylsulfonylamino, thienylmethylsulfonylamino pyridylmethylsulfonylamino, furylmethylsulfonylamino, thienylethylsulfonylamino, pyridylethylsulfonylamino, furylethylsulfonylamino, thienylpropylsulfonylamino, pyridylbutylsulfonylamino, furylpentylsulfonylamino or thienylhexylsulfonylamino group, or said groups having a C$_1$–C$_6$ alkyl group on the aromatic ring.

A is a group which forms together with the adjacent carbon-carbon double bond a 5- or 6-membered heteroaromatic ring including 1 to 4 hetero atoms selected from the group consisting of a nitrogen atom, an oxygen atom and a sulfur atom (provided that optional 1 or 2 hydrogen atoms on the heteroaromatic ring may be replaced with a hydroxyl group, an amino group, a C$_1$–C$_6$ alkoxy group, a C$_1$–C$_6$ alkylthio group, a halogen atom, a cyano group, a nitro group, a mono- or di-C$_1$–C$_6$ alkylamino group which may be substituted by a hydroxyl group at the alkyl moiety, a C$_3$–C$_8$ cycloalkylamino group which may be substituted by a hydroxyl group at the alkyl or alkylene moiety, a C$_3$–C$_8$ cycloalkyl C$_1$–C$_6$ alkylamino group which may be substituted by a hydroxyl group at the alkyl or alkylene moiety, an N—(C$_1$–C$_6$alkyl)—N—(C$_3$–C$_8$ cycloalkyl)amino group which may be substituted by a hydroxyl group at the alkyl or alkylene moiety, an N—(C$_1$–C$_6$ alkyl)—N—(aroyl) amino group which may be substituted by a hydroxyl group at the alkyl moiety, a C$_4$–C$_7$ cyclic imino group which may be substituted by a hydroxyl group at the alkylene moiety, a carboxyl group, a C$_1$–C$_6$ alkoxycarbonyl group, a formyl group, a C$_2$–C$_6$ alkanoyl group, an aroyl group, or a C$_1$–C$_6$ alkyl group, C$_3$–C$_8$ cycloalkyl group, C$_3$–C$_8$ cycloalkyl C$_1$–C$_6$ alkyl group, C$_2$–C$_6$ alkenyl group or C$_2$–C$_6$ alkynyl group which may be substituted by 1 to 3 substituents selected from the group consisting of a hydroxyl group, an amino group, a C$_1$–C$_6$ alkoxy group and a mono- or di-C$_1$–C$_6$ alkylamino group, and when the heteroaromatic ring includes one or more nitrogen atoms, the nitrogen atom(s) may be oxidized to form an N-oxide group).

The C$_1$–C$_6$ alkoxy group means a linear or branched alkoxy group having 1 to 6 carbon atoms such as a methoxy, ethoxy, propoxy, isopropoxy, butoxy, isobutoxy, sec-butoxy, tert-butoxy, pentyloxy or hexyloxy group.

The C$_1$–C$_6$ alkylthio group means a linear or branched alkylthio group having 1 to 6 carbon atoms such as a methylthio, ethylthio, propylthio, isopropylthio, butylthio, isobutylthio, sec-isobutylthio, tert-butylthio, pentylthio or hexylthio group.

The halogen atom means a fluorine, chlorine, bromine or iodine atom.

The mono-or di-alkylamino group wherein an optional hydrogen atom(s) at the alkyl moiety may be replaced with a hydroxyl group means a linear or branched alkylamino group having, at the nitrogen, 1 or 2 linear or branched alkyl groups which may be substituted by a hydroxyl group, such as a methylamino, ethylamino, propylamino, isopropylamino, butylamino, isobutylamino, tert-butylamino, pentylamino, isopentylamino, hexylamino, dimethylamino, ethylmethylamino, diethylamino, dipropylamino, propylmethylamino, ethylpropylamino, diisopropylamino, diisobutylamino, ethylisobutylamino, di-tert-butylamino, dipentylamino, di isopentylamino, isopentylmethylamino or dihexylamino group.

The C$_3$–C$_8$ cycloalkylamino group wherein an optional hydrogen atom(s) at the alkyl or alkylene moiety may be replaced with a hydroxyl group means a C$_3$–C$_8$ cycloalkylamino group which may be substituted by a hydroxyl group at the alkyl or alkylene moiety, such as a cyclopropylamino, cyclobutylamino, cyclopentylamino, cyclohexylamino, cyclooctylamino, 2-methylcyclopropylamino, 1-methylcyclobutylamino, 2-methylcyclopentylamino or 2,2-dimethylcyclohexylamino.

The $C_3$–$C_8$ cycloalkyl $C_1$–$C_6$ alkylamino group wherein an optional hydrogen atom(s) at the alkyl or alkylene moiety may be replaced with a hydroxyl group means a $C_3$–$C_8$ cycloalkyl $C_1$–$C_6$ alkylamino group which has 4 to 14 carbon atoms and may be substituted by a hydroxyl group at the alkyl or alkylene moiety, such as a cyclopropylmethylamino, cyclobutylmethylamino, cyclopentylmethylamino, cyclohexylmethylamino, cycloheptylmethylamino, cyclooctylmethylamino, 1-cyclopropylethylamino, 2-cyclopropylethylamino, 3-cyclopropylpropylamino, 2-cyclobutylethylamino or 2-cyclopentylethylamino group.

The N—($C_1$–$C_6$ alkyl)—N—($C_3$–$C_8$ cycloalkyl 1)amino group wherein an optional hydrogen atom(s) at the alkyl or alkylene moiety may be replaced with a hydroxyl group means an N—($C_1$–$C_6$ alkyl)—N—($C_3$–$C_8$ cycloalkyl)amino group which has 4 to 15 carbon atoms and may be substituted by a hydroxyl group at the alkyl or alkylene moiety, such as an N-methyl-N-cyclopropylamino, N-methyl-N-cyclobutylamino, N-methyl-N-cyclopentylamino, N-methyl-N-cyclohexylamino, N-methyl-N-cyclooctylamino, N-ethyl-N-cyclopropylamino, N-butyl-N-cyclopropylamino, N-pentyl-N-cyclopropylamino, N-hexyl-N-cyclopropylamino, N-ethyl-N-cyclobutylamino, N-ethyl-N-cyclopentylamino, N-propyl-N-cyclobutylamino, N-pentyl-N-cyclopentylamino group.

The N—($C_1$–$C_6$ alkyl)-N-(aroyl)amino group wherein an optional hydrogen atom(s) at the alkyl moiety may be replaced with a hydroxyl group means an N—($C_1$–$C_6$ alkyl)-N-(aroyl)amino group which has 6 to 12 carbon atoms and may be substituted by a hydroxyl group at the alkyl moiety, such as an N-methyl-N-benzoylamino, N-(1-ethyl)-N-benzoylamino, N-(1-propyl)-N-benzoylamino, N-(1-butyl)-N-benzoylamino, N-(1-pentyl-N-benzoylamino, N-(2-ethyl)-N-benzoylamino, N-(2-propyl)-N-benzoylamino, N-(3-butyl-N-benzoylamino, N-(4-pentyl)-N-benzoylamino, N-methyl-N-naphthoylamino, N-methyl-N-thienylcarbonylamino, N-methyl-N-furylamino, N-methyl-N-pyridylamino or N-methyl-N-imidazoylamino group.

The $C_4$–$C_7$ cyclic imino group wherein an optional hydrogen atom(s) may be replaced with a hydroxyl group means a cyclic imino group which has 4 to 7 carbon atoms and may be substituted by a hydroxyl group at the alkylene moiety, such as a 1-pyrrolidinyl, 2-methylpyrrolidino, 2,5-dimethylpyrrolidino, piperidino, 2-methylpiperidino, 2,6-dimethylpiperidino, morpholino, thiomorpholino, piperazino, 4-methylpiperazino or hexamethyleneimino group.

The $C_1$–$C_6$ alkoxycarbonyl group means an alkoxycarbonyl group having a linear or branched $C_1$–$C_6$ alkoxy group such as a methoxycarbonyl, ethoxycarbonyl, propoxycarbonyl, isopropoxycarbonyl, butyloxycarbonyl, isobutyloxycarbonyl, tert-butyloxycarbonyl, pentyloxycarbonyl, isopentyloxycarbonyl or hexyloxycarbonyl group.

The $C_2$–$C_6$ alkanoyl group means a linear or branched alkanoyl group having 2 to 6 carbon atoms such as an acetyl, propanoyl, butylyl, isobutylyl, isopropanoyl, isobutylyl, pentanoyl or hexanoyl group.

The aroyl group means an aroyl group having mono-, bi- or tri-cyclic aromatic hydrocarbon ring or heteroaromatic ring including 1 to 4 hetero atoms selected from the group consisting of an oxygen atom, a nitrogen atom and a sulfur atom, such as a benzoyl, naphthoyl, pyridylcarbonyl, thienylcarbonyl, furylcarbonyl, thiazolylcarbonyl, oxazolylcarbonyl, imidazolylcarbonyl or quinolylcarbonyl group.

The $C_1$–$C_6$ alkyl group means a linear or branched alkyl group having 1 to 6 carbon atoms such as a methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl or 1-ethyl-1-methylpropyl group.

The $C_3$–$C_8$ cycloalkyl group means a cycloalkyl group having 3 to 8 carbon atoms such as a cyclopropyl, cyclobutyl, cyclopentyl, cyclohexyl, cycloheptyl or cyclooctyl group.

The $C_2$–$C_6$ alkenyl group means a linear or branched alkenyl group having 2 to 6 carbon atoms such as a vinyl, allyl, 2-propenyl, isopropenyl, 3-butenyl, 2-butenyl, 1-butenyl, 1-methyl-2-propenyl, 1-methyl-1-propenyl, 1-ethyl-1-ethenyl, 2-methyl-2-propenyl, 2-methyl-1-propenyl or 4-pentenyl group.

The $C_3$–$C_8$ cycloalkyl $C_1$–$C_6$ alkyl group means a $C_1$–$C_6$ alkyl group substituted by a $C_3$–$C_8$ cycloalkyl group such as a cyclopropylmethyl, 1-cyclopropylethyl, 2-cyclopropylethyl, 2-cyclopropylpropyl, 3-cyclopropylpropyl, 4-cyclopropylbutyl, 5-cyclopropylpenyl, 6-cyclopropylhexyl, cyclobutylmethyl, 1-cyclobutylethyl, 2-cyclobutylethyl, cyclopentylmethyl, cyclohexylmethyl, cycloheptylmethyl or cyclooctylmethyl group.

The $C_2$–$C_6$ alkynyl group means a linear or branched alkynyl group having 2 to 6 carbon atoms such as a ethynyl, 1-propynyl, 2-propynyl, 1-butynyl, 2-butynyl, 3-butynyl, 1-methyl-2-propynyl or 1-pentynyl group.

A is a group which forms together with the adjacent carbon-carbon double bond a 5- or 6-membered heteroaromatic ring including 1 to 4 hetero atoms selected from the group consisting of a nitrogen atom, an oxygen atom and a sulfur atom, and examples of the 5- or 6-membered heteroaromatic ring are a furan ring, a pyrrole ring, a thiophene ring, a diazole ring, a thiazole ring, an oxazole ring, a pyridine ring, a diazine ring, a triazine ring, etc.

Preferred compounds useful in the present invention are those wherein A is a group which forms together with the adjacent carbon-carbon double bond a 5- or 6-membered nitrogen-containing aromatic ring or the corresponding N-oxide ring (provided that optional 1 or 2 hydrogen atoms on the heteroaromatic ring may be replaced with a hydroxyl group, an amino group, a $C_1$–$C_6$ alkoxy group, a $C_1$–$C_6$ alkylthio group, a mono- or di-$C_1$–$C_6$ alkylamino group which may be substituted by a hydroxyl group at the alkyl moiety, a $C_3$–$C_8$ cycloalkylamino group which may be substituted by a hydroxyl group at the alkyl or alkylene moiety, a $C_3$–$C_8$ cycloalkyl $C_1$–$C_6$ alkylamino group which may be substituted by a hydroxyl group at the alkyl or alkylene moiety, an N—($C_1$–$C_6$ alkyl)—N—($C_3$–$C_8$ cycloalkyl)amino group which may be substituted by a hydroxyl group at the alkyl or alkylene moiety, an N—($C_1$–$C_6$ alkyl)-N-(aroyl)amino group which may be substituted by a hydroxyl group at the alkyl moiety, a $C_4$–$C_7$ cyclic imino group which may be substituted by a hydroxyl group at the alkylene moiety, or a $C_1$–$C_6$ alkyl group, $C_3$–$C_8$ cycloalkyl group, $C_3$–$C_8$ cycloalkyl $C_1$–$C_6$ alkyl group, $C_2$–$C_6$ alkenyl group or $C_2$–$C_6$ alkynyl group which may be substituted by 1 to 3 groups selected from the group consisting of a hydroxyl group, an amino group, a $C_1$–$C_6$ alkoxy group and a mono- or di-$C_1$–$C_6$ alkylamino group).

Specific examples of the endothelin antagonists useful in the present invention include 6-Ethoxycarbonyl-5-(3,4-methylenedioxyphenyl)-7-(4-methoxyphenyl)cyclopenteno[1,2-b]pyridine,
(5RS,6SR,7SR)-6-Carboxy-5-(3,4-methylenedioxyphenyl)-7-(4-methoxyphenyl)cyclopenteno[1,2-b]pyridine,
6-Ethoxycarbonyl-5,7-diphenylcyclopenteno[1,2-b]pyridine,
(5RS,6SR,7SR)-6-Carboxy-5,7-diphenylcyclopenteno [1,2-b]pyridine,
6-Ethoxycarbonyl-5,7-di(4-methoxyphenyl)cyclopenteno [1,2-b]pyridine,
(5RS,6SR,7SR)-6-Carboxy-5,7-di(4-methoxyphenyl) cyclopenteno[1,2-b]pyridine,
6-Ethoxycarbonyl-5,7-di(3,4-methylenedioxyphenyl) cyclopenteno[1,2-b]pyridine,
(5RS,6SR,7SR)-6-Carboxy-5,7-di(3,4-methylenedioxyphenyl)cyclopenteno[1,2-b]pyridine,
6-Ethoxycarbonyl-7-(3,4-methylenedioxyphenyl)-5-(4-methoxyphenyl)-7-(3,4-methylenedioxyphenyl) cyclopenteno[1,2-b]pyridine,
(5RS,6SR,7SR)-6-Carboxy-7-(3,4-methylenedioxyphenyl)-5-(4-methoxyphenyl)cyclopenteno[1,2-b]pyridine,
6-Ethoxycarbonyl-5-phenyl-7-(4-methoxyphenyl) cyclopenteno[1,2-b]pyridine,
(5RS,6SR,7SR)-6-Carboxy-5-phenyl-7-(4-methoxyphenyl) cyclopenteno[1,2-b]pyridine,
6-Ethoxycarbonyl-7-phenyl-5-(4-methoxyphenyl) cyclopenteno[1,2-b]pyridine,
(5RS,6SR,7SR)-6-Carboxy-7-phenyl-5-(4-methoxyphenyl) cyclopenteno[1,2-b]pyridine,
6-Ethoxycarbonyl-5-phenyl-7-(3,4-methylenedioxyphenyl) cyclopenteno[1,2-b]pyridine,
(5RS,6SR,7SR)-6-Carboxy-5-phenyl-7-(3,4-methylenedioxyphenyl)cyclopenteno[1,2-b]pyridine,
6-Ethoxycarbonyl-7-phenyl-5-(3,4-methylenedioxyphenyl) cyclopenteno[1,2-b]pyridine,
(5RS,6SR,7SR)-6-Carboxy-7-phenyl-5-(3,4-methylenedioxyphenyl)cyclopenteno[1,2-b]pyridine,
(5RS,6SR,7SR)-6-Carboxy-7-(3,4-methylenedioxyphenyl)-5-(4-methoxyphenyl)cyclopenteno[1,2-c]pyridine,
(5RS,6SR,7SR)-6-Carboxy-5-(3,4-methylenedioxyphenyl)-7-(4-methoxyphenyl)cyclopenteno[1,2-c]pyridine,
(5RS,6SR,7SR)-6-Carboxy-2-propoxy-5-(3,4-methylenedioxyphenyl)-7-(4-methoxyphenyl) cyclopentenol[1,2-b]pyridine,
(5RS,6SR,7SR)-6-Carboxy-2-methyl-5-(3,4-methylenedioxyphenyl)-7-(4-methoxyphenyl) cyclopenteno[1,2-b]pyridine,
(5RS,6SR,7SR)-6-Carboxy-2-butyl-5-(3,4-methylenedioxyphenyl)-7-(4-methoxyphenyl) cyclopenteno[1,2-b]pyridine,
(5RS,6SR,7SR)-6-Carboxy-2-ethylaminomethyl-5-(3,4-methylenedioxyphenyl)-7-(4-methoxyphenyl) cyclopenteno[1,2-b]pyridine,
(5RS,6SR,7SR)-6-Carboxy-5-(3,4-methylenedioxyphenyl)-7-(4-methoxyphenyl)cyclopenteno[1,2-b]pyridine, N-oxide
(5RS,6SR,7SR)-6-Carbamoyl-5-(3,4-methylenedioxyphenyl)-7-(4-methoxyphenyl)cyclopenteno[1,2-b] pyridine,
(5RS,6SR,7SR)-6-Methanesulfonylaminocarbonyl-5-(3,4-methylenedioxyphenyl)-7-(4-methoxyphenyl) cyclopenteno[1,2-b]pyridine,
(5RS,6SR,7SR)-6-(4-Isopropylbenzenesulfonylaminocarbonyl)-5-(3,4-methylenedioxyphenyl)-7-(4-methoxyphenyl) cyclopenteno[1,2-b]pyridine,
6-Carboxy-5-hydroxy-5-(3,4-methylenedioxyphenyl)-7-(4-methoxyphenyl)cyclopent-1,4-dieno[1,2-b]pyridine,
(5RS,6SR,7SR)-6-Carboxy-7-(2-carboxymethoxy-4-methoxyphenyl)-5-(3,4-methylenedioxyphenyl) cyclopenteno[1,2-b]pyridine,
(5RS,6SR,7RS)-6-carboxy-5-(2-carboxymethoxy-4-methoxyphenyl)-7-(3,4-methylenedioxyphenyl) cyclopenteno[1,2-c]pyridine,
(5RS,6SR,7SR)-6-carboxy-7-(2-hydroxy-4-methoxyphenyl)-5-(3,4-methylenedioxyphenyl) cyclopenteno[1,2-b]pyridine,
(5RS,6SR,7SR)-6-carboxy-7-[2-(2-hydroxyethoxy)-4-methoxyphenyl]-5-(3,4-methylenedioxyphenyl) cyclopenteno[1,2-b]pyridine,
(5RS,6SR,7SR)-6-carboxy-7-[2-(2-methylaminoethoxy)-4-methoxyphenyl]-5-(3,4-methylenedioxyphenyl)-cyclopenteno[1,2-b]pyridine,
(5RS,6SR,7SR)-6-Carboxy-2-ethoxymethyl-7-(4-methoxyphenyl)-5-(3,4-methylenedioxyphenyl) cyclopenteno[1,2-b]pyridine,
(5RS,6SR,7SR)-6-Carboxy-7-(4-methoxyphenyl)-5-(3,4-methylenedioxyphenyl)-2-propylcyclopenteno[1,2-b] pyridine,
(5RS,6SR,7SR)-6-Carboxy-2-isobutyl-7-(4-methoxyphenyl)-5-(3,4-methylenedioxyphenyl) cyclopenteno[1,2-b]pyridine,
6-Carboxy-7-hydroxy-7-(4-methoxyphenyl)-5-(3,4-methylenedioxyphenyl)cyclopent-1,3-dieno[1,2-b] pyridine,
6-Carboxy-5-hydroxy-7-(4-methoxyphenyl)-5-(3,4-methylenedioxyphenyl)-2-propylcyclopent-1,3-dieno[2,1-b]pyridine,
(5RS,6SR,7RS)-6-Carboxy-5-hydroxy-7-(4-methoxyphenyl)-5-(3,4-methylenedioxyphenyl) cyclopenteno[1,2-b]pyridine,
(5RS,6SR,7SR)-6-Carboxy-7-(4-hydroxyphenyl)-5-(3,4-methylenedioxyphenyl)cyclopenteno[1,2-b]pyridine,
(5RS,6SR,7RS)-6-Carboxy-7-[4-(2-hydroxyethoxy) phenyl]-5-(3,4-methylenedioxyphenyl)cyclopenteno[1,2-b]-pyridine,
(5RS,6SR,7SR)-6-Carboxy-7-[4-(2-methylaminoethoxy) phenyl]-5-(3,4-methylenedioxyphenyl)cyclopenteno[1,2-b]-pyridine,
(5RS,6SR,7SR)-6-Carboxy-7-(4-hydroxymethyl-phenyl)-5-(3,4-methylenedioxyphenyl)cyclopenteno[1,2-b] pyridine,
(5RS,6SR,7SR)-6-Carboxy-5-(3,4-methylenedioxyphenyl)-7-(3-thienyl)cyclopenteno[1,2-b]pyridine,
(5RS,6SR,7RS)-7-(4-Methoxyphenyl)-5-(3,4-methylenedioxyphenyl)-6-(2-oxo-3H-1,2,3,5-oxathiadiazol-4-yl)cyclopenteno[1,2-b]pyridine,
(5RS,6SR,7SR)-6-(5-Oxo-4H-1,2,4-oxadiazol-3-yl)-5-(3,4-methylenedioxyphenyl)-7-(4-methoxyphenyl) cyclopenteno[1,2-b]pyridine,
(5RS,6SR,7SR)-6-(Tetrazol-5-yl)-5-(3,4-methylenedioxyphenyl)-7-(4-methoxyphenyl) cyclopenteno[1,2-b]pyridine,
(5RS,6SR,7SR)-5-(3,4-methylenedioxyphenyl)-6-methoxycarbonyl-7-(4-methoxyphenyl)cyclopenteno[1,2-b]pyridine,
(5RS,6SR,7SR)-7-(2-Ethoxycarbonylmethoxy-4-methoxyphenyl)-6-Carboxy-5-(3,4-methylenedioxyphenyl)cyclopenteno[1,2-b]pyridine, (5RS,6SR,7SR)-6-Carboxy-7-[2-(tetrazol-5-ylaminocarbonylmethoxy)-4-methoxyphenyl]-5-(3,4-methylendioxyphenyl)cyclopenteno[1,2-b]pyridine, (5RS,6SR,7SR)-7-(2-Carbamoylmethoxy-4-methoxyphenyl)-6-carboxy-5-(3,4-methylendioxyphenyl)cyclopenteno[1,2-b]pyridine, (5RS,6SR,7SR)-6-Carboxy-7-(2-methanesulfonyl-aminocarbonylmethoxy-4-methoxyphenyl)-5-(3,4-methylenedioxyphenyl)cyclopenteno[1,2-b]pyridine, (5RS,6SR,7SR)-6-Carboxy-7-[2-(tetrazol-5-ylmethoxy)-4-methoxyphenyl]-5-(3,4-methylenedioxyphenyl)cyclopenteno[1,2-b]pyridine, (5RS,6SR,7SR)-6-Carboxy-7-[2-(1-methoxycarbonylpropoxy)-4-methoxyphenyl]-5-(3,4-methylenedioxyphenyl)cyclopenteno[1,2-b]pyridine, (5RS,6SR,7SR)-6-Carboxy-7-[2-(1-methoxycarbonylpropoxy)-4-methoxyphenyl]-5-(3,4-methylenedioxyphenyl)cyclopenteno[1,2-b]pyridine, (5RS,6SR,7SR)-6-Carboxy-7-[2-(1-carboxy propoxy)-4-methoxyphenyl]-5-(3,4-methylenedioxyphenyl)cyclopenteno[1,2-b]pyridine, (5RS,6SR,7SR)-6-Carboxy-7-[2-(1-carboxypropoxy)-4-methoxyphenyl]-5-(3,4-methylendioxyphenyl)cyclopenteno[1,2-b]pyridine, (5RS,6SR,7SR)-7-[2-(1-ethoxycarbonyLethoxy)-4-methoxyphenyl]-6-carboxy-5-(3,4-methylenedioxyphenyl)cyclopenteno[1,2-b]pyridine, (5RS,6SR,7SR)-6-Carboxy-7-[2-(1-carboxyethoxy)-4-methoxyphenyl]-5-(3,4-methylenedioxyphenyl)cyclopenteno[1,2-b]pyridine, (5RS,6SR,7SR)-6-Carboxy-7-[2-(2-carboxyethoxy)-4-methoxyphenyl]-5-(3,4-methylenedioxyphenyl)cyclopenteno[1,2-b]pyridine, (5RS,6SR,7SR)-6-Carboxy-7-[2-[2-(2-carboxyethoxycarbonyl)ethoxy]-4-methoxyphenyl]5-(3,4-methylenedioxyphenyl)cyclopenteno[1,2-b]pyridine, (5RS,6SR,7SR)-6-Carboxy-7-[2-[2-(2-carboxyethoxycarbonyl)ethoxycarbonyl]ethoxy]-4-methoxyphenyl]-5-(3,4-methylenedioxyphenyl)cyclopenteno[1,2-b]pyridine, (5RS,6SR,7SR)-6-Carboxy-7-[2-(2-benzyloxy-1-methoxycarbonylethoxy)-4-methoxyphenyl]-5-(3,4-methylenedioxyphenyl)cyclopenteno[1,2-b]pyridine, (5RS,6SR,7SR)-6-Carboxy-7-[2-(1-methoxycarbonylethenyloxy)-4-methoxyphenyl]-5-(3,4-methylenedioxyphenyl)cyclopenteno[1,2-b]pyridine, (5RS,6SR,7SR)-6-Carboxy-7-[2-(2-hydroxy-1-methoxycarbonylethoxy)-4-methoxyphenyl]-5-(3,4-methylenedioxyphenyl)cyclopenteno[1,2-b]pyridine, (5RS,6SR,7SR)-6-Carboxy-7-[2-(1-carboxy-2-hydroxyethoxy)-4-methoxyphenyl]-5-(3,4-methylenedioxyphenyl)cyclopenteno[1,2-b]pyridine, (5RS,6SR,7SR)-6-Carboxy-7-[2-(1-carboxyethenyloxy)-4-methoxyphenyl]-5-(3,4-methylenedioxyphenyl)cyclopenteno[1,2-b]pyridine, (5RS,6SR,7SR)-6-Carboxy-2-hydroxymethyl-5-(3,4-methylenedioxyphenyl)-7-(4-methoxyphenyl)cyclopenteno[1,2-b]pyridine, (5RS,6SR,7SR)-2-Ethoxymethyl-6-carboxy-7-(2-carboxymethoxy-4-methoxyphenyl)-5-(3,4-methylenedioxyphenyl)cyclopenteno[1,2-b]pyridine, (5RS,6SR,7SR)-7-(2-Ethylaminocarbonylmethoxy-4-methoxyphenyl)-2-ethylaminomethyl-6-carboxy-5-(3,4-methylenedioxyphenyl)cyclopenteno[1,2-b]pyridine, (5RS,6SR,7SR)-2-Ethylaminomethyl-6-carboxy-7-(2-carboxymethoxy-4-methoxyphenyl)-5-(3,4-methylenedioxyphenyl)cyclopenteno[1,2-b]pyridine, (5RS,6SR,7SR)-6-Carboxy-7-(2-carboxylmethoxy-4-methoxyphenyl)-2-propoxy-5-(3,4-methylenedioxyphenyl)cyclopenteno[1,2-b]pyridine, (5RS,6SR,7SR)-2-Ethyl-6-carboxy-5-(3,4-methylenedioxyphenyl)-7-(4-methoxyphenyl)cyclopenteno[1,2-b]pyridine, (5RS,6SR,7SR)-6-Carboxy-2-cyclopropyl-5-(3,4-methylenedioxyphenyl)-7-(4-methoxyphenyl)cyclopenteno[1,2-b]pyridine, (5RS,6SR,7SR)-6-Carboxy-2-pentyl-5-(3,4-methylenedioxyphenyl)-7-(4-methoxyphenyl)cyclopenteno[1,2-b]pyridine, 6-Carboxy-5-hydroxy-2-(3-butenyl)-5-(3,4-methylenedioxyphenyl)-7-(4-methoxyphenyl)cyclopent-1,3-dieno[2,1-b]pyridine, (5RS,6SR,7SR)-6-Carboxy-2-(3-butenyl)-5-(3,4-methylenedioxyphenyl)-7-(4-methoxyphenyl)cyclopenteno[1,2-b]pyridine, (5RS,6SR,7SR)-6-Carboxy-2-propylthio-5-(3,4-methylenedioxyphenyl)-7-(4-methoxyphenyl)cyclopenteno[1,2-b]pyridine, (5RS,6SR,7SR)-6-carboxy-2-propylamino-5-(3,4-methylenedioxyphenyl)-7-(4-methoxyphenyl)cyclopenteno[1,2-b]pyridine, (5RS,6SR,7SR)-6-Carboxy-2-piperidino-5-(3,4-methylenedioxyphenyl)-7-(4-methoxyphenyl)cyclopenteno[1,2-b]pyridine, (5RS,6SR,7SR)-2-butyl-6-Carboxy-7-(2-carboxymethoxy4-methoxyphenyl)-5-(3,4-methylenedioxyphenyl)cyclopenteno[1,2-b]pyridine, (5RS,6SR,7SR)-6-Carboxy-7-(2-carboxymethoxy-4-methoxyphenyl)-2-propylamino-5-(3,4-methylenedioxyphenyl)cyclopenteno[1,2-b]pyridine, (5RS,6SR,7SR)-6-Carboxy-7-(2-carboxymethylamino-4-methoxyphenyl)-5-(3,4-methylenedioxyphenyl)cyclopenteno[1,2-b]pyridine, (5RS,7SR)-6-Ethoxycarbonyl-7-(2-carboxymethylamino-4-methoxyphenyl)-5-(3,4-methylenedioxyphenyl)cyclopenteno[1,2-b]pyridine, (5RS,6SR,7SR)-6-Carboxy-7-(2-pyridyl)-5-(3,4-methylenedioxyphenyl)cyclopenteno[1,2-b]pyridine, (5RS,6SR,7SR)-6-Carboxy-5-(3-fluorophenyl)-7-(4-methoxyphenyl)cyclopenteno[1,2-b]pyridine, (5RS,6SR,7SR)-6-Carboxy-5-(3-methoxyphenyl)-7-(4-methoxyphenyl)cyclopenteno[1, 2-b]pyridine, (5RS,6SR,7SR)-6-Carboxy-7-(4-fluorophenyl)-5-(3,4-methylenedioxyphenyl)-cyclopenteno[1,2-b]pyridine, (5RS,6SR,7SR)-6-Carboxy-5-(2-methoxyphenyl)-7-(4-methoxyphenyl)cyclopenteno[1,2-b]pyridine, (5RS,6SR,7SR)-7-[2-(5-Oxo-4H-1,2,4-oxadiazol-3-ylmethoxy)-4-methoxyphenyl]-6-carboxy-5-(3,4-methylenedioxyphenyl)cyclopenteno[1,2-b]pyridine, 6-Carboxy-5-hydroxy-5-(3,4-methylenedioxyphenyl)-7-(4-methoxyphenyl)cyclopent-1,3-dieno[2,1-d]pyridine 6-Carboxy-5-hydroxy-2-butyl-5-(3,4-methylenedioxyphenyl)-7-(methoxyphenyl)cyclopent-1,3-dieno[2,1-d]pyrimidine (5RS,6SR,7SR)-6-Carboxy-7-(2-(1-carboxypentyloxy)-4-methoxyphenyl)-5-(3,4-methylenedioxyphenyl)cyclopenteno[1,2-b]pyridine, (5RS,6SR,7SR)-6-Carboxy-7-[2-[(E)-2-carboxyethenyl]-4-methoxyphenyl]-5-(3,4-methylenedioxyphenyl)cyclopenteno[1,2-b]pyridine, (5RS,6SR,7SR)-6-Carboxy-5-(3,4-methylenedioxyphenyl)-7-[2-(2-methoxycarbonylethyl)-4-methoxyphenyl]cyclopenteno[1,2-b]pyridine, (5RS,6SR,7SR)-6-Carboxy-7-[2-(2-carboxyethyl)-4-methoxyphenyl]-5-(3,4-methylenedioxyphenyl)cyclopenteno[1,2-b]pyridine, (5RS,6SR,7SR)-6-Carboxy-5-(3,4-methylenedioxyphenyl)-7-[2-(2-methoxycarbonylpropyl)-4-methoxyphenyl]cyclopenteno[1,2-b]pyridine, (5RS,6SR,7SR)-6-Carboxy-7-[2-(2-carboxypropyl)-4-methoxyphenyl]-5-(3,4-methylenedioxyphenyl)cyclopenteno[1,2-b]pyridine, (5RS,6SR,7SR)-6-Carboxy-5-(3,4-methylenedioxyphenyl)-7-[2-(2-carboxy-2-propenyl)-4-methoxyphenyl]cyclopenteno[1,2-b]pyridine, (5RS,6SR,7SR)-6-Carboxy-7-[2-(2-carboxy-2-propenyl)-4-methoxyphenyl]-5-(3,4-methylenedioxyphenyl)cyclopenteno[1,2-b]pyridine, (5RS,6SR,7SR)-6-Carboxy-7-[2-(1,2-dihydroxy-2-methoxycarbonylethyl)-4-methoxyphenyl]-5-(3,4-methylenedioxyphenyl)cyclopenteno[1,2-b]pyridine, (5RS,6SR,7SR)-6-Carboxy-7-[2-(2-carboxy-1,2-dihydroxyethyl)-4-methoxyphenyl]-5-(3,4-methylenedioxyphenyl)cyclopenteno[1,2-b]pyridine, (5RS,6SR,7SR)-6-Carboxy-7-[2-(3-hydroxy-1-propynyl)-4-methoxyphenyl]-5-(3,4-methylenedioxyphenyl)cyclopenteno[1,2-b]pyridine, (5RS,6SR,7SR)-6-Carboxy-7-[2-[(Z)-(3-hydroxy-1-propenyl)-4-methoxyphenyl]-5-(3,4-methylenedioxyphenyl)cyclopenteno[1,2-b]pyridine, (5RS,6SR,7SR)-6-Carboxy-7-[2-[(E)-(3-hydroxy-1-propenyl)]-4-methoxyphenyl]-5-(3,4-methylenedioxyphenyl)cyclopenteno[1,2-b]pyridine, (5RS,6SR,7SR)-6-Carboxy-7-(2-(3-hydroxypropyl)-4-methoxyphenyl]-5-(3,4-methylenedioxyphenyl)cyclopenteno[1,2-b]pyridine, (5RS,6SR,7SR)-6-Carboxy-7-[2-(1,2-dihydroxyethyl)-4-methoxyphenyl]-5-(3,4-methylenedioxyphenyl)cyclopenteno[1,2-b]pyridine, (5RS,6SR,7SR)-6-Carboxy-7-[2-(1,3-dihydroxypropyl)-4-methoxypheny]-5-(3,4-methylenedioxyphenyl)cyclopenteno[1,2-b]pyridine, (5RS,6SR,7SR)-6-Carboxy-7-[2-(2,3-dihydroxypropyl)-4-methoxypheny]-5-(3,4-methylenedioxyphenyl)cyclopenteno[1,2-b]pyridine, (5RS,6SR,7SR)-6-Carboxy-7-[2-(1,2,3-trihydroxypropyl)-4-methoxypheny]-5-(3,4-methylenedioxyphenyl)cyclopenteno[1,2-b]pyridine, (5RS,6SR,7SR)-6-Carboxy-7-[2-(1,2,3-trihydroxypropyl)-4-methoxypheny]-5-(3,4-methylenedioxyphenyl)cyclopenteno[1,2-b]pyridine, (5RS,6SR,7SR)-6-Carboxy-7-[2-1-carboxy-2-hydroxyethoxy)-4-methoxyphenyl]-2-propylamino-5-(3,4-methylenedioxyphenyl)cyclopenteno[1,2-b]pyridine, (5RS,6SR,7SR)-6-Carboxy-7-[2-(1-carboxyethenyloxy)-4-methoxyphenyl]-2-propylamino-5-(3,4-methylenedioxyphenyl)cyclopenteno[1,2-b]pyridine, (5RS,6SR,7SR)-7-(2-Ethoxycarbonylmethoxy-4-methoxyphenyl)-6-carboxy-2-(N-propyl-N-methylamino)-5-(3,4-methylenedioxyphenyl)cyclopenteno[1,2-b]pyridine, (5RS,6SR,7SR)-6-Carboxy-7-(2-carboxymethoxy-4-methoxyphenyl)-2-(N-propyl-N-methylamino)-5-(3,4-methylenedioxyphenyl)cyclopenteno[1,2-b]pyridine, (5RS,6SR,7SR)-6-Carboxy-7-(2-carboxymethoxy-4-methoxyphenyl)-2-methylamino)-5-(3,4-methylenedioxyphenyl)cyclopenteno[1,2-b]pyridine, (5RS,6SR,7SR)-6-Carboxy-7-(2-carboxymethoxy-4-methoxyphenyl)-2-(N,N-dimethylamino)-5-(3,4-methylenedioxyphenyl)cyclopenteno[1,2-b]pyridine, (5RS,6SR,7SR)-6-Carboxy-7-(2-carboxymethoxy-5-tert-butyl-4-methoxyphenyl)-2-methylamino-5-(3,4-methylenedioxyphenyl)cyclopenteno[1,2-b]pyridine, (5RS,6SR,7SR)-2-Amino-6-carboxy-7-(2-carboxymethoxy-4-methoxyphenyl)-5-(3,4-methylenedioxyphenyl)cyclopenteno[1,2-b]pyridine, (5RS,6SR,7SR)-6-Carboxy-7-(2-carboxymethoxy-4-methoxyphenyl)-2-[(N-benzoyl)-3-hydroxypropylamino]-5-(3,4-methylenedioxyphenyl)cyclopenteno[1,2-b]pyridine, (5RS,6SR,7SR)-6-Carboxy-7-(2-carboxymethoxy-4-methoxyphenyl)-2-(3-hydroxypropylamino)-5-(3,4-methylenedioxyphenyl)cyclopenteno[1,2-b]pyridine, (5RS,6SR,7SR)-6-Carboxy-7-(2-carboxymethoxy-4-methoxyphenyl)-2-(2-hydroxyethylamino)-5-(3,4-methylenedioxyphenyl)cyclopenteno[1,2-b]pyridine, (5RS,6SR,7SR)-6-Carboxy-5-(3,5-dimethoxyphenyl)-7-(4-methoxypheny)cyclopenteno[1,2-b]pyridine, (5RS,6SR,7SR)-6-Carboxy-5-(3-propoxy-5-methoxyphenyl)-7-(4-methoxyphenyl)cyclopenteno[1,2-b]pyridine, (5RS,6SR,7SR)-6-Carboxy-5-(3,4-methylenedioxy-5-methoxyphenyl)-7-(4-methoxyphenyl)cyclopenteno[1,2-b]pyridine, (5RS,6SR,7SR)-6-Carboxy-5-(3-benzyloxy-4-methoxyphenyl)-7-(4-methoxyphenyl)cyclopenteno[1,2-b]pyridine, (5RS,6SR,7SR)-6-Carboxy-5-(3-hydroxy-4-methoxyphenyl)-7-(4-methoxypheny)cyclopenteno[1,2-b]pyridine, (5RS,6SR,7SR)-5-(4-Indolyl)-6-carboxy-7-(4-methoxyphenyl)cyclopenteno[1,2-b]pyridine, (5RS,6SR,7SR)-7-(5-Indolyl)-6-carboxy-5-(3,4-methylenedioxyphenyl)cyclopenteno[1,2-b]pyridine, (5RS,6SR,7SR)-7-(4-Ethoxyphenyl)-6-carboxy-5-(3,4-methylenedioxyphenyl)cyclopenteno[1,2-b]pyridine, (5RS,6SR,7SR)-7-[2-(4-imidazolylmethoxy)-4-methoxyphenyl]-6-carboxy-5-(3,4-methylenedioxyphenyl)cyclopenteno[1,2-b]pyridine, (5RS,6SR,7SR)-7-[2-(2-Oxo-4,5-dihydrofuryloxy)-4-methoxyphenyl]-6-carboxy-5-(3,4-methylenedioxyphenyl)cyclopenteno[1,2-b]pyridine, (5RS,6SR,7SR)-6-Carboxy-7-[2-(1-carboxy-3-hydroxypropoxy)-4-methoxyphenyl]-5-(3,4-methylenedioxyphenyl)cyclopenteno[1,2-b]pyridine, (5RS,6SR,7SR)-7-(2-Acetoxymethylcarbonylmethoxy-4-methoxyphenyl-6-carboxy-5-(3,4-methylenedioxyphenyl)cyclopenteno[1,2-b]pyridine, (5RS,6SR,7SR)-2-Isopropylamino-6-carboxy-5-(3,4-methylenedioxyphenyl-7-(4-methoxyphenyl)cyclopenteno[1,2-b]pyridine, 6-Carboxy-5-(3,4-methylenedioxyphenyl-7-(4-methoxyphenyl)cyclopent-1,2-dieno[1,2-b]pyridine, 6-Carboxy-5-(3,4-methylenedioxyphenyl-7-(4-methoxyphenyl)cyclopent-1,2-dieno[2,1-b]pyridine, (5RS,6SR,7SR)-6-Carboxy-2,7-dimethyl-5-(3,4-methylenedioxyphenyl-7-(4-methoxyphenyl)cyclopenteno[1,2-b]pyridine, (5RS,6SR,7SR)-6-Carboxy-2-pyrrolidino-5-(3,4-methylenedioxyphenyl-7-(4-methoxyphenyl)cyclopenteno[1,2-b]pyridine, (5RS,6SR,7SR)-6-Carboxy-7-(2,3-dihydro-5-benzofuranyl)-5-(3,4-methylenedioxyphenyl)cyclopenteno[1,2-b]pyridine, (5RS,6SR,7SR)-6-Carboxy-7-[2-(2-hydroxyethoxy)-4-methoxyphenyl]-2-(N-methyl-3-hydroxypropylamino)-5-(3,4-methylenedioxyphenyl)cyclopenteno[1,2-b]pyridine, (5RS,6SR,7SR)-6-Carboxy-2-cyclopropylamino-5-(3,4-methylenedioxyphenyl)-7-(4-methoxphenyl)cyclopenteno[1,2-b]pyridine, (5RS,6SR,7SR)-6-Carboxy-2-(N-methylisopropylamino)-5-(3,4-methylenedioxyphenyl)-7-(4-methoxphenyl)cyclopenteno(1,2-b]pyridine,
(5RS,6SR,7SR)-6-Carboxy-2-(N-methylcyclopropylamino)-5-(3,4-methylenedioxyphenyl)-7-(4-methoxphenyl)cyclopenteno[1,2-b]pyridine,
(5RS,6SR,7SR)-2-Ethylamino-6-carboxy-7-[2-(2-carboxyethyl-4-methoxyphenyl)-5-(3,4-methylenedioxyphenyl)cyclopenteno[1,2-b]pyridine,
(5RS,6SR,7SR)-6-Carboxy-7-[2-(2-carboxy-2-propenyl)-4-methoxyphenyl]-2-propylamino-5-(3,4-methylenedioxyphenyl)cyclopenteno[1,2-b]pyridine,
(5RS,6SR,7SR)-6-Carboxy-7-[2-(2-carboxypropyl)-4-methoxyphenyl]-2-propylamino-5-(3,4-methylenedioxyphenyl)cyclopenteno[1,2-b]pyridine,
(5RS,6SR,7SR)-6-Carboxy-5-(3,4-methylenedioxyphenyl)-7-(2-(3-methoxypropyl)-4-methoxyphenyl]cyclopenteno[1,2-b]pyridine,
(5RS,6SR,7SR)-7-[2-(2-Acetoxymethylcarbonylethyl)-4-methoxyphenyl]-6-carboxy-5-(3,4-methylenedioxyphenyl)cyclopenteno[1,2-b]pyridine,
(5RS,6SR,7SR)-6-Carboxy-7-[2-(2-hydroxymethylcarbonylethyl)-4-methoxyphenyl]-5-(3,4-methylenedioxyphenyl)cyclopenteno[1,2-b]pyridine,
(5RS,6SR,7SR)-6-Carboxy-7-[2-(3-carboxypropyl)-4-methoxyphenyl]-5-(3,4-methylenedioxyphenyl)cyclopenteno[1,2-b]pyridine,
(5RS,6SR,7SR)-6-Carboxy-7-[2-(3-carboxy-2-propylmethyl)-4-methoxyphenyl]-5-(3,4-methylenedioxyphenyl)cyclopenteno[1,2-b]pyridine,
(5RS,6SR,7SR)-6-Carboxy-7-[2-(2-carboxypropyl)-4-methoxyphenyl]-2-isopropylamino-5-(3,4-methylenedioxyphenyl)cyclopenteno[1,2-b]pyridine,
(5RS,6SR,7SR)-6-Carboxy-7-[2-(2-carboxy-3-hydroxypropyl)-4-methoxyphenyl]-2-propylamino-5-(3,4-methylenedioxyphenyl)cyclopenteno[1,2-b]pyridine,
(5RS,6SR,7SR)-2-Ethylamino-6-carboxy-7-[2-(2-carboxypropyl)-4-methoxyphenyl]-5-(3,4-methylenedioxyphenyl)cyclopenteno[1,2-b]pyridine,
(5RS,6SR,7SR)-2-Isobutylamino-6-carboxy-7-[2-(2-carboxypropyl)-4-methoxyphenyl]-5-(3,4-methylenedioxyphenyl)cyclopenteno[1,2-b]pyridine,
(5RS,6SR,7SR)-6-Carboxy-7-[2-(2-carboxypropyl)-4-methoxyphenyl-]2-cyclopentylamino-5-(3,4-methylenedioxyphenyl)cyclopenteno[1,2-b]pyridine,
(5RS,6SR,7SR)-6-Carboxy-7-[2-(2-carboxypropyl)-4-methoxyphenyl]-2-[N-(methyl)propylamino]-5-(3,4-methylenedioxyphenyl)cyclopenteno[1,2-b]pyridine,
(5RS,6SR,7SR)-6-Carboxy-7-[2-(2-carboxypropyl)-4-methoxyphenyl]-2-[N-(methyl)isopropylamino]-5-(3,4-methylenedioxyphenyl)cyclopenteno[1,2-b]pyridine,
(5RS,6SR,7SR)-6-Carboxy-7-[2-(2-carboxypropyl)-4-methoxyphenyl]-2-[N-(methyl)ethylamino]-5-(3,4-methylenedioxyphenyl)cyclopenteno[1,2-b]pyridine,
(5RS,6SR,7SR)-6-Carboxy-7-[2-(2-carboxy-2-hydroxypropyl)-4-methoxyphenyl]-2-[N-(methyl)propylamino]-5-(3,4-methylenedioxyphenyl)cyclopenteno[1,2-b]pyridine,
(5RS,6SR,7SR)-6-Carboxy-7-[2-(2-carboxyethyl)-4-methoxyphenyl]-2-(N,N-diethylamino)-5-(3,4-methylenedioxyphenyl)cyclopenteno[1,2-b]pyridine,
(5RS,6SR,7SR)-6-Carboxy-7-[2-(2-carboxyethyl)-4-methoxyphenyl]-2-[N-(ethyl)propylamino]-5-(3,4-methylenedioxyphenyl)cyclopenteno[1,2-b]pyridine,
(5RS,6SR,7SR)-6-Carboxy-7-[2-(2-carboxypropyl)-4-methoxyphenyl]-2-(N,N-diethylamino)-5-(3,4-methylenedioxyphenyl)cyclopenteno[1,2-b]pyridine,
(5RS,6SR,7SR)-6-Carboxy-7-[2-(2-carboxypropyl)-4-methoxyphenyl]-2-[N-(ethyl)propylamino]-5-(3,4-methylenedioxyphenyl)cyclopenteno[1,2-b]pyridine,
(5RS,6SR,7SR)-6-Carboxy-7-[2-(2-carboxypropyl)-4-methoxyphenyl]-2-pyrrolidino-5-(3,4-methylenedioxyphenyl)cyclopenteno[1,2-b]pyridine,
(5RS,6SR,7SR)-2-(4-Hydroxybutylamino)-5-(3,4-methylenedioxyphenyl)-6-methoxycarbonyl-7-[2-(2-methoxycarbonylpropyl-4-methoxyphenyl]cyclopenteno(1,2-b]pyridine,
(5RS,6SR,7SR)-2-Isobutyl-6-carboxy-7-[2-(2-carboxypropyl)-4-methoxyphenyl]-5-(3,4-methylenedioxyphenyl)cyclopenteno[1,2-b]pyridine,
(5RS,6SR,7SR)-2-Butyl-6-carboxy-7-[2-(2-carboxypropyl)-4-methoxyphenyl]-5-(3,4-methylenedioxyphenyl)cyclopenteno[1,2-b]pyridine,
(5RS,6SR,7SR)-6-Carboxy-7-[2-(2-carboxypropyl)-4-methoxyphenyl]-2-cyclopentyl-5-(3,4-methylenedioxyphenyl)cyclopenteno[1,2-b]pyridine,
(5RS,6SR,7SR)-6-Carboxy-7-[2-(2-carboxypropyl)-4-methoxyphenyl]-2-[N-(methyl)isopropylamino]-5-(3,4-methylenedioxyphenyl)cyclopenteno[1,2-b]pyridine,
(5RS,6SR,7SR)-6-Carboxy-7-[2-(2-carboxypropyl)-4-methoxyphenyl]-2-[N-(ethyl)isopropylamino]-5-(3,4-methylenedioxyphenyl)cyclopenteno[1,2-b]pyridine,
(5RS,6SR,7SR)-7-(2-(2-Carboxypropyl)-4-methoxyphenyl]-5-(3,4-methylenedioxyphenyl)-6-methoxycarbonylcyclopenteno[1,2-b]pyridine,
(5RS,6SR,7SR)-6-Carboxy-7-[2-(2-carboxy-3-hydroxypropyl)-4-methoxyphenyl]-2-propylamino-5-(3,4-methylenedioxyphenyl)cyclopenteno[1,2-b]pyridine,
(5RS,6SR,7SR)-6-Carboxy-7-[2-(2-carboxy-3hydroxypropyl)-4-methoxyphenyl]-2-[N -(methyl)propylamino]-5-(3,4-methylenedioxyphenyl)cyclopenteno[1,2-b]pyridine,
(5RS,6SR,7SR)-6-Carboxy-7-[2-(2-carboxyethyl)-4-methoxyphenyl]-2-[N-(methyl)ethylamino-5-(3,4-methylenedioxyphenyl)cyclopenteno[1,2-b]pyridine,
(5RS,6SR,7SR)-2-Sec-butylamino-6-carboxy-7-[2-(2-carboxypropyl)-4-methoxyphenyl]-5-(3,4-methylenedioxyphenyl)cyclopenteno[1,2-b]pyridine,
(5RS,6SR,7SR)-6-Carboxy-7-[2-(3-carboxy-2-methylpropyl)-4-methoxyphenyl]-2-propylamino-5-(3,4-methylenedioxyphenyl)cyclopenteno[1,2-b]pyridine,
(5RS,6SR,7SR)-6-Tert-butoxycarbonyl-7-[2-(2-methoxycarbonyl-2-propenyl)-4-methoxyphenyl]-5-(3,4-methylenedioxyphenyl)-5-(3,4-methylenedioxyphenyl)cyclopenteno[1,2-b]pyridine,
(5RS,6SR,7SR)-2-(1-Ethylpropylamino)-6-carboxy-7-[2-(2-carboxypropyl)-4-methoxyphenyl]-5-(3,4-methylenedioxyphenyl)cyclopenteno[1,2-b]pyridin
(5RS,6SR,7SR)-6-Carboxy-7-[2-(2-carboxypropyl)-4-methoxyphenyl]-2-tert-butylamino-5-(3,4-methylenedioxyphenyl)cyclopenteno[1,2-b]pyridine,
(5RS,6SR,7SR)-6-Carboxy-7-[2-(2-carboxy-2-propenyl)-4-methoxyphenyl]-2-isopropylamino-5-(3,4-methylenedioxyphenyl)cyclopenteno[1,2-b]pyridine,
(5RS,6SR,7SR)-6-Carboxy-7-[2-(2-carboxypropyl)-4-methoxyphenyl]-2-cyclohexylamino-5-(3,4-methylenedioxyphenyl)cyclopenteno[1,2-b]pyridine, and isomerically pure compounds and pharmaceutically acceptable salts thereof.

Preferred are (5RS, 6SR,7SR-2-butyl-6-carboxy-7-[2-(2-carboxypropyl)-4-methoxyphenyl]-5-(3,4-methylenedioxyphenyl)cyclopenteno[1,2-b]pyridine and (5RS,6SR,7SR)-2-isopropylamino-6-carboxy-7-[2-(2- carboxypropyl)-4-methoxyphenyl]-5-(3,4-methylenedioxyphenyl)cyclopenteno[1,2-b]pyridine, and isomerically pure compounds thereof.

Especially preferred are most potent endothelin antagonistic isomers selected from the group consisting of (5R,6S,7S)-2-butyl-6-carboxy-7-[(R)-2-(2-carboxypropyl)-4-methoxyphenyl]-5-(3,4-methylenedioxyphenyl)cyclopenteno[1,2-b]pyridine, (5R,6S,7S)-2-butyl-6-carboxy-7-[(S)-2-(2-carboxypropyl)-4-methoxyphenyl]-5-(3,4-methylenedioxyphenyl)cyclo-penteno[1,2-b]pyridine, (5S,6R,7R)-2-butyl-6carboxy-7-[(R)-2-(2-carboxypropyl)-4-methoxyphenyl]-5-(3,4 -methylenedioxyphenyl)cyclopenteno[1,2-b]pyridine, (5S,6R,7R)-2-butyl-6-carboxy-7-[(S)-2-(2-carboxypropyl)-4-methoxyphenyl]-5-(3,4-methylenedioxyphenyl)cy-clopenteno[1,2-b]pyridine, (5R,6S,7S)-2-isopropylamino-6-carboxy-7-[(R)-2-(2-carboxypropyl)-4-methoxyphenyl]-5-(3,4-methylenedioxyphenyl)cyclopenteno[1,2-b]pyridine, (5R,6S,7S)-2-isopropylamino-6-carboxy-7-[(S)-2-(2-carboxypropyl)-4-methoxyphenyl]-5-(3,4-methylenedioxyphenyl)cyclopenteno[1,2-b]pyridine, (5S,6R,7R)-2-isopropylamino-6-carboxy-7-[(R)2-(2-carboxypropyl)-4-methoxyphenyl]-5-(3,4-methylenedioxyphenyl)cyclopenteno[1,2 -b]pyridine and (5S,6R,7R)-2-isopropylamino-6-carboxy-7-[(S)-2-(2-carboxypropyl)-4-methoxyphenyl]-5-(3,4-methylenedioxyphenyl)cyclopenteno[1,2-b]pyridine.

The above-described compounds form salts with various inorganic and organic acids and bases and these salts are also within the scope of the invention. Such salts include ammonium salts, alkali metal salts like sodium and potassium salts, alkaline earth metal salts like calcium and magnesium salts, salts with organic bases; e.g., dicyclohexylamine salts, N-methyl-D-glucamine, salts with amino acids like arginine, lysine and the like. Also, salts with organic and inorganic acids may be prepared: e.g., HCl, HBr, $H_2SO_4$, $H_3PO_4$, methanesulfonic, toluenesulfonic, maleic, fumaric, camphorsulfonic.

The compounds described above are disclosed in WO95/05374, the disclosure of which is incorpoared herein by reference, and can be prepared by the methods described therein. Isomerically pure compounds thereof can be prepared from the corresponding isomeric mixture, for example, by means of chromatography using chiral column.

The above endothelin antagonist compounds of Formula I, including their pharmaceutically acceptable salts are effective in the prevention and/or treatment of heart failure (i.e. congestive heart failure) and ventricular dysfunction (symptomatic and asymptomatic). Among the compounds of Formula I useful in the treatment of heart failure and ventricular dysfunction is an isomeric mixture of (5RS, 6SR, 7SR)-2-butyl-6-carboxy-7-[2-(2-carboxypropyl)-4-methoxyphenyl]-5-(3,4-methylenedioxyphenyl)-cyclopenteno[1,2-b]pyridine. This isomeric mixture was chromatographed using a chiral column and the most active isomer (+)-, (5S*, 6R* , 7R*)-2-butyl-6-carboxy-7-[2-(2-carboxypropyl)-4-methoxyphenyl]-5-(3,4-methylenedioxyphenyl)cyclopenteno[1,2-b]pyridine, hereinafter referred to as Compound 1, was identified and isolated. See Example 1.

The instant invention relates to a method of preventing and/or treating heart failure and ventricular dysfunction, including but not limited to congestive heart failure, in a warm blooded animal which comprises administering to the warm blooded animal in need of such treatment a therapeutically effective amount of a compound of Formula I. Additionally, the administration of an endothelin antagonist for the treatment of heart failure and ventricular dysfunction a) may cause regression (i.e. reversal) of heart failure and ventricular dysfunction; b) may prevent histologic/morphologic changes in end organs, such as heart, vasculature and kidney associated with heart failure and ventricular dysfunction; and c) may also manage secondarily any of the following conditions renal failure, atrial flutter, atrial fibrillation and ventricular arrhythmia.

For the purposes of this disclosure, a warm blooded animal is a member of the animal kingdom possessed of a homeostatic mechanism, and includes mammals and birds. Preferably the warm blooded animal is man. A therapeutically effective amount, for the purposes of this disclosure, is an amount effective to improve cardiac function and/or reduce the hemodynamic burden on the heart and/or alleviate other pathophysiologic manifestations of heart failure and ventricular dysfunction.

The endothelin antagonistic substances above described may be used in the form of drug formulations suitable for parenteral administration, oral administration or external administration by mixing them with solid or liquid excipient carriers known in this field. The drug formulations include a liquid formulation such as an injection formulation, an inhalant formulation, a syrup formulation or an emulsion, a solid formulation such as tablets, capsules or granules, and an external drug such as an ointment or a suppository. Further, these drug formulations may contain additives which are commonly employed, such as an adjuvant, a stabilizer, a wetting agent, an emulsifier, an absorption-promoting agent or a surfactant, as the case requires. As the additives, distilled water for injection, physiological saline, Ringer's solution, glucose, sugar syrup, gelatin, vegetable oil, cacao butter, ethylene glycol, hydroxypropyl cellulose, lactose, sucrose, corn starch, magnesium stearate and talc may be mentioned.

The dose of an endothelin antagonist varies depending upon the manner of administration, the age and body weight of the patient and the condition of the patient to be treated. However, a typical administration method for an adult is oral administration or parenteral administration. The daily dose in the case of oral administration to an adult patient is from 0.1 to 100 mg/kg body weight, and the daily dose in the case of parenteral administration is from 0.01 to 10 mg/kg body weight.

The following Examples illustrate the present invention more specifically. It should be understood that the present invention is not limited to these examples alone.

EXAMPLE 1

(+)-(5S*, 6R*, 7R*)-2-butyl-6-carboxy-7-[2-(2-carboxypropyl)-4-methoxyphenyl]-5-(3,4-methylenedioxyphenyl)cyclopenteno[1,2-b]pyridine Separation of (+) and (−) compound obtained in Example 186 of WO95/05374 was done by a HPLC column (Daicel chiralpack AD); retention time for (+) 39–58 min,
HPLC data:
column chiralpak AD (Daicel), 50 mm diameter, 500 mm length;
solvent hexane:isopropanol:TFA (90:10:0.1);
flow rate 100 ml/min;
injection 1.1 g of racemate in isopropanol;
detection UV=260 nm The above separation was repeated eight times and the fractions containing the desired compound were combined and evaporated to dryness. To the residue were added AcOEt and water. The aqueous phase was adjusted to pH 4 with 3N NaOH. The organic phase was washed with water, brine, and dried over $Na_2SO_4$. The solvent was removed under reduced pressure, and the residue was purified by column chromatography on silica gel (Wako Gel®C-300, eluent; hexane (2)/AcOEt(1)→AcCEt) to give a glassy solid (2.91 g). The solid was triturated in water to afford a title compound as white amorphous powder (2.24g).

$^1$H-NMR (300 MHz, $CDCl_3$, δ ppm); 0.84 (3H, t, J=7.3 Hz), 1.18–1.35 (2H, m), 1.31 (3H, d, J=6.3 Hz), 1.40–1.56 (2H, m), 2.55–2.72 (3H, m), 2.88–3.02 (1H, m), 3.36 (1H, dd, J=5.6 Hz, 13.1 Hz), 3.60 (1H, t, J=9.7 Hz), 3.75 (3H, s), 4.58 (1H, d, J=9.7 Hz) m, 4.99 (1H, d, J=9.7 Hz), 6.00 (2H, br s), 6.70 (1H, d, J=2.7 Hz), 6.775 (1H, d, J=1.4 Hz), 6.785 (1H, dd, J=2.7 Hz, 8.6 Hz), 6.81 (1H, dd, J=1.4 Hz, 7.9 Hz), 6.84 (1H, d, J-7.9 Hz), 6.94 (1H, d, J=8.6 Hz),7.06 (1H, d, J=7.9 Hz), 7.33 (1H, d, J=7.9 Hz)

$[α]_D20=+46.1°$ c=1, $CH_3OH$)

Rf value: 0.40 (E. Merck, Kieselgel 60 F $_{254}$/chloroform)

The $^{isomerically}$ pure compound is hereinafter designated as Compound 1.

EXAMPLE 2
Step A: Implantation of Instrumentation

Figure 8:
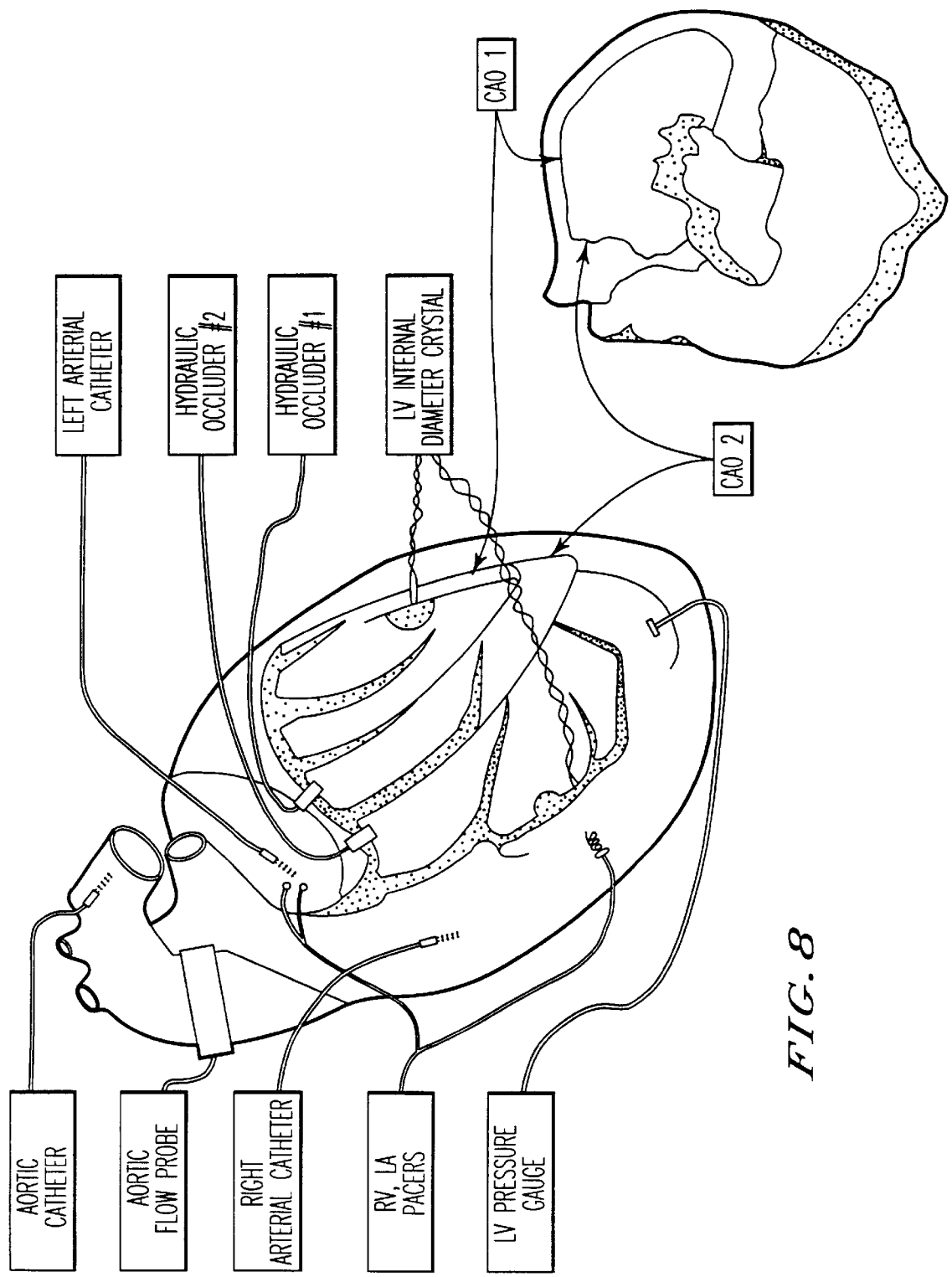

Five farm pigs of either of sex and weighing 34.5±2.5 kg were sedated with ketamine hydrochloride (25 mg/kg, i.m.) and xylazine (6 mg/kg, i.m.). After tracheal intubation, general anesthesia was maintained with isoflurane (1.5–2.0 vol % in oxygen). Using sterile surgical technique, a left thoracotomy was performed at the fifth intercostal space. Catheters made of Tygon tubing (Norton Performance Plastics Co., Akron, Ohio) were implanted in the descending aorta, left and right atria for measurement of pressures. A solid-state miniature pressure gauge (Konigsberg Instruments Inc., Pasadena, Calif.) was implanted in the left ventricular (LV) chamber to obtain LV pressure and the rate of change of LV pressure (LV dP/dt). A flow probe (Transonic System Inc., Ithaca, N.Y.) was placed around the main pulmonary artery for measurement of blood flow. One pair of piezoelectric ultrasonic dimension crystals were implanted on opposing anterior and posterior endocardial regions of the LV to measure the short-axis internal diameter. Proper alignment of the endocardial crystals was achieved during surgical implantation by positioning the crystals so as to obtain a signal with the greatest amplitude and shortest transit time. A pacing lead (model 5069, Medtronic Inc., Minneapolis, Minn.) was attached to the right ventricular free wall, and stainless steel pacing leads were attached to the left atrial appendage. The left circumflex coronary artery was isolated and two hydraulic occluders, made of Tygon tubing, were implanted proximally and distally to the first obtuse marginal branch. The wires and catheters were externalized between the scapulae, the incision was closed in layers, and air was evacuated from the chest cavity. See FIG. 8.

Step B: Experimental Measurements

Hemodynamic recordings were made using a data tape recorder (RD-130TE, TEAC, Montebello, Calif.) and a multiple-channel oscillograph (MT95K2, Astro-Med, West Warwick, R.I.). Aortic and left atrial pressures were measured using strain gauge manometers (Statham Instruments, Oxnard, Calif.), which were calibrated in vitro using a mercury manometer, connected to the fluid-filled catheters. The solid-state LV pressure gauge was cross-calibrated with aortic and left atrial pressure measurements. LV dP/dt was obtained by electronically differentiating the LV pressure signal. Blood flow was measured using a volume flow meter (T208, Transonic System Inc., Ithaca, N.Y.). Mean arterial pressure, left atrial pressures, and pulmonary blood flow (cardiac output) were measured using an amplifier filter. Stroke volume was calculated as the quotient of cardiac output and heart rate. Cardiac output was normalized by body weight to yield cardiac index. LV dimension was measured with an ultrasonic transit-time dimension gauge (Model 203, Triton Technology Inc., San Diego, Calif.). Total peripheral resistance was calculated as the quotient of mean arterial pressure and cardiac output. LV short-axis end-diastolic dimension (EDD) was measured at the beginning of the upstroke of the LV dP/dt signal. LV end-systolic dimension (ESD) was measured at the time of maximum negative dP/dt. The percent shortening of LV internal diameter was calculated as (EDD-ESD)/EDD*100. LV mean velocity of circumferential fiber shortening (Vcf) was calculated from the dimension measurements using the following formula:(EDD-ESD)/EDD/Ejection time ($sec^{-1}$). Ejection time was measured as the interval between maximum and minimum LV dP/dt. A cardiotachometer triggered by the LV pressure pulse provided instantaneous and continuous records of heart rate.

Step C: Heart Failure Model

Experiments were initiated 10–14 days after surgery, when the pigs were fully recovered from surgery. During the post-operative period, the pigs were introduced to a sling for training. Heart failure was produced by progressive myocardial ischemia induced by two coronary artery occlusions followed by intermittent ventricular pacing. Briefly, after post-surgical hemodynamic control monitoring was performed, the left circumflex coronary artery was occluded by inflating the distally implanted hydraulic occluder. Approximately 48 hrs after the first occlusion, the proximal coronary artery occluder was inflated. Ore to two days following the second myocardial infarction, the right ventricle was paced at a rate of 190–210 beats/min using a programmable external cardiac pacemaker (model EV4543, Pace Medical, Waltham, Me.). Pacing was continued for 1 week and then terminated for 3 days. This procedure was repeated another 1–2 cycles, until heart failure was evident and the hemodynamic parameters were stable.

Step D: Experimental Protocols

Hemodynamic experiments were performed after 2 cycles of tachycardic pacing in the presence of myocardial ischemia injury, after the animal had achieved a stable state of heart failure. During the experiments, the pigs were conscious and quietly restrained in a sling. The test compound is dissolved in saturated $NaHCO_3$ (10% by Vol) and 0.9% saline (90% by Vol) at a concentration of 2 mg/ml, was studied in four conscious pigs with heart failure. A dose of 0.5 mg/kg was injected intravenously over a period of 2 minutes, and hemodynamics were continuously recorded before and 90 minutes following injection of the test compound in all 4 pigs. In two of these pigs, recording continued until 3 hours following injection of the test compound. The vehicle was tested on separate days. The effects of 0.1 to 0.5 μg/kg cumulative bolus doses in 0.1 μg/kg steps of endothelin-1 (Peptide Institute, Inc., Osaka, Japan) were also examined on separate days before and 90 minutes after injection of the test compound in three pigs during development of heart failure to characterize the extent of endothelin block by the test compound. ET-1 was dissolved in 0.1 N $NaHCO_3$ (95% by Vol) and 0.9% saline (95% by Vol) at a concentration of 20 μg/ml.

Step E: Data Analysis

All data were stored on an AST 4/d computer. Data before and after development of heart failure were compared using Student', t-test for paired data. The data at baseline and after injection of the test compound also were compared using Student's t-test for paired data with a Bonferroni correction. All values are expressed as the mean ±S.E. Statistical significance was accepted at the p<0.05 level.

EXAMPLE 3

Experimental protocol using an endothelin antagonist: Compound 1

Step A: Hemodynamic study with Compound 1

Hemodynamic experiments were performed after 2 cycles of tachycardic pacing in the presence of myocardial ischemia injury, after the animal had achieved a stable state of heart failure. During the experiments, the pigs were conscious and quietly restrained in a sling. Compound 1, dissolved in saturated $NaHCO_3$ (10% by Vol) and 0.9% saline (90% by Vol) at a concentration of 2 mg/ml, was studied in four conscious pigs with heart failure. A dose of 0.5 mg/kg was injected intravenously over a period of 2 minutes, and hemodynamics were continuously recorded before and 90 minutes following injection of Compound 1 in all 4 pigs. In two of these pigs, recording continued until 3 hour following injection of Compound 1. The vehicle was tested on separate days. The effects of 0.1 to 0.5 µg/kg cumulative bolus doses in 0.1 µg/kg steps of endothelin-1 (Peptide Institute, Inc., Osaka, Japan) were also examined on separate days before and 90 minutes after injection of Compound 1 in three pigs during development of heart failure to characterize the extent of ET block by Compound 1. ET-1was dissolved in 0.1 N $NaHCO_3$ (95% by Vol) and 0.9% saline (95% by Vol) at a concentration of 20 µg/ml. For comparative purpose, the effects of intravenous injection of Compound 2 (enalaprilat), at doses of 1 mg/kg and 4 mg/kg, were studied on different days in three of the pigs that were used to study Compound 2 and in one additional pig. Compound 2 was dissolved in 0.9% saline.

Step B: Baseline Hemodynamics Before and After Development of Heart Failure

Tables 1 and 2 summarize the baseline LV function and systemic vascular dynamics before (i.e., post surgical control) and after heart failure induced by serial myocardial infarctions in combination with intermittent tachycardic stress in conscious pigs. Heart failure resulting from at least 2 cycles of tachycardic pacing in the presence of myocardial injure was manifested by significant increases in LV end-diastolic (+10.7±0.4 mm from 40.2±3.6 mm) and end-systolic diameters (+14.6±1.1 mm from 31.2±2.7 mm) and in mean left atrial pressure (+19±3 mmHg from 4±2 mmHg). LV dP/dt, LV fractional shortening, Vcf, and cardiac index significantly decreased by 45±4, 54±6, 46±1 and 29±8%, respectively. Also, total peripheral resistance increased significantly (+46±14%), while mean arterial pressure and heart rate were unchanged. In addition to these hemodynamic changes, which are shown in FIGS. 1 and 2, heart failure, particularly at the advanced stages, was characterized by anorexia, peripheral and pulmonary edema, and reduced activity.

TABLE 1

Baseline Left Ventricular Function in Controls and Conscious Pigs with Heart Failure.

|  | Control | Heart Failure |
|---|---|---|
| LV End-Diastolic Diameter (mm) | 40.2 ± 3.6 | 50.9 ± 3.5* |
| LV End-Systolic Diameter (mm) | 31.2 ± 2.7 | 45.8.± 3.6* |
| LV Fractional Shortening (%) | 22.3 ± 1.5 | 10.3 ± 1.3* |

TABLE 1-continued

Baseline Left Ventricular Function in Controls and Conscious Pigs with Heart Failure.

|  | Control | Heart Failure |
|---|---|---|
| Vcf ($sec^{-1}$) | 1.1 ± 0.1 | 0.6 ± 0.0* |
| LV dP/dt (mmHg/sec) | 3012 ± 153 | 1681 ± 184* |

*Significantly different from control, p < 0.05.
Data are mean ± SE with n = 3, except that LV dP/dt n = 4.

TABLE 2

Baseline Cardiac and Systemic Hemodynamics in Controls and Conscious Pigs with Heart Failure.

|  | Control | Heart Failure |
|---|---|---|
| Mean Arterial Pressure (mmHg) | 90 ± 3 | 88 ± 5 |
| Mean Left Atrial Pressure (mmHg) | 4 ± 2 | 23 ± 3* |
| Cardiac Index (ml/min/kg) | 123 ± 11 | 86 ± 9* |
| Total Peripheral Resistance (mmHg/ml/min/kg) | 0.73 ± 0.06 | 1.04 ± 0.09 |
| Heart Rate (beat/min) | 139 ± 4 | 143 ± 15 |

*Significantly different from control, p < 0.05.
Data are mean ± SE with n = 4.

Step C: Effects Compound 1 on Hemodynamics in Heart Failure

The time course of hemodynamic changes following intravenous administration of Compound 1 (0.5 mg/kg) are shown in FIGS. 3 and 4. Tables 3 and 4 summarize LV function and systemic hemodynamic responses to Compound 1 at 15 minutes and 60 minutes after administration of Compound 1. FIGS. 1 and 2 illustrate the cardiac and systemic dynamic measurements made before and after development of heart failure, as well as 60 minutes after administration of Compound 1 during the heart failure stage.

Compound 1 mainly induced a sustained increase in cardiac index, and prolonged decreases in mean arterial pressure and total peripheral resistance. For example, at 60 minutes after administration of Compound 1, mean arterial pressure was significantly decreased by 10±2% and cardiac index was increased by 17±4%. Thus, total peripheral resistance was significantly decreased by 22±3% with Compound 1, which basically constitutes a complete restoration of the elevated vascular resistance of heart failure back to pre-heart failure control values (FIG. 1). Although Compound 1 also decreased left atrial pressure and increased heart rate, these changes were not statistically significant. Vcf was increased by 12±2%, while LV dP/dt, LV end-diastolic and systolic diameter, and LV fraction shortening were not affected by Compound 1. The vehicle did not induce any significant changes throughout 180 minutes of observation (FIGS. 3 and 4).

The salutary effects of acute administration of Compound 1 in this heart failure model were predominantly due to the reversal of elevated vascular resistance.

TABLE 3

Effects of Intravenous Injection of Compound 1 (0.5 mg/kg)
on LV Function in Conscious Pigs with Heart Failure

| | | Change from Baseline | |
|---|---|---|---|
| | BaseLine | 15 min | 60 min |
| LV End-Diastolic Diameter (mm) | 50.9 ± 3.5 | +0.1 ± 0.2 | +0.2 ± 0.3 |
| LV End-Systolic Diameter (mm) | 45.8 ± 3.6 | −0.3 ± 0.3 | −0.2 ± 0.3 |
| LV Fractional Shortening (%) | 10.3 ± 1.3 | +0.6 ± 0.2 | +0.7 ± 0.2 |
| Vcf (sec$^{-1}$) | 0.60 ± 0.04 | 0.05 ± 0.01* | +0.07 ± 0.02* |
| LV dP/dt (mmHg/sec) | 1681 ± 184 | +25 ± 40 | 56 ± 65 |

*Significantly different from baseline, p < 0.025.
Data are mean ± SE with n = 3, except that LV dP/dt n = 4.

TABLE 4

Effects of Intravenous Injection of Compound 1 (0.5 mg/kg)
on Cardiac and Systemic Hemodynamics in Conscious Pigs
with Heart Failure.

| | | Change from Baseline | |
|---|---|---|---|
| | Baseline | 15 min | 60 min |
| Left Atrial Pressure (mmHg) | 23 ± 3 | −4 ± 2 | −2 ± 2 |
| Mean Arterial Pressure (mmHg) | 88 ± 5 | −10 ± 1* | −8 ± 1* |
| Cardiac Index (ml/min/kg) | 86 ± 9 | +14 ± 2* | +13 ± 2* |
| Total Peripheral Resistance (mmHg/ml/min/kg) | 1.04 ± 0.09 | −0.25 ± 0.03* | −0.24 ± 0.05 |
| Heart Rate beat/min | 143 ± 15 | +5 ± 5 | +7 ± 5 |

*Significantly different from baseline, p < 0.025.
Data are mean ± SE with n = 4.

Step D: Effects of Compound 1 Compared with Compound 2 in Heart Failure

Figure 5:
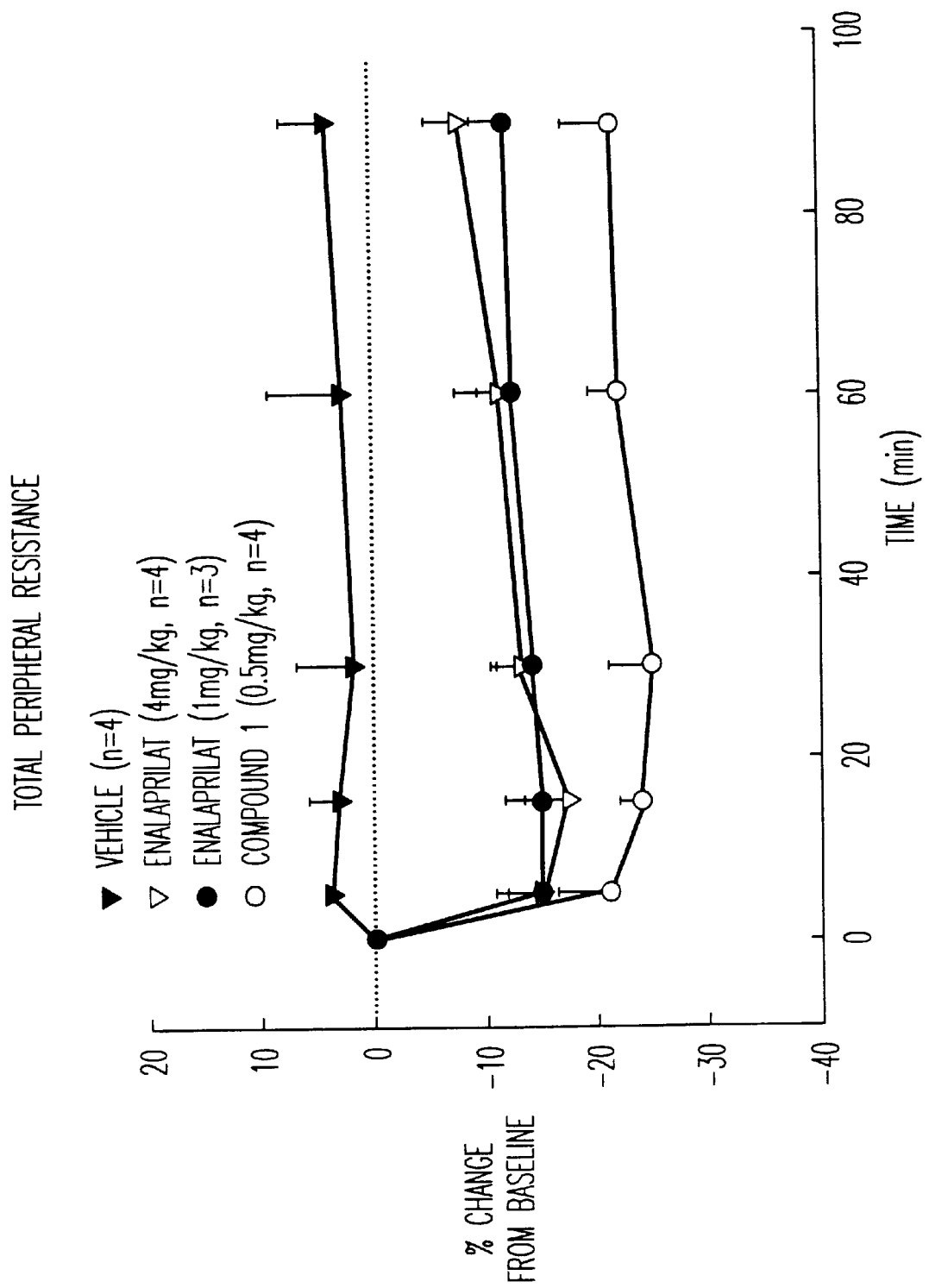
Figure 6:
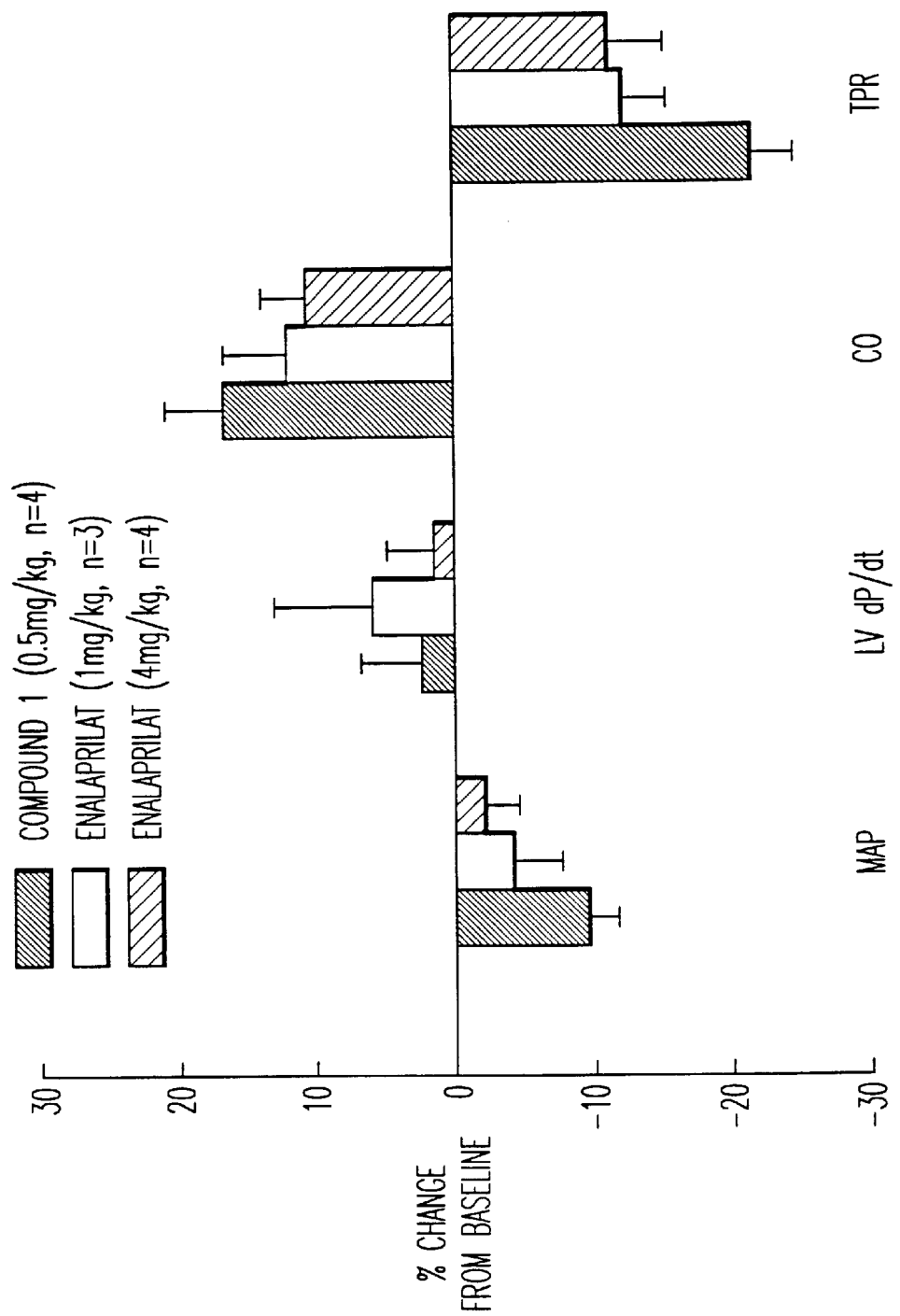
Figure 7A:
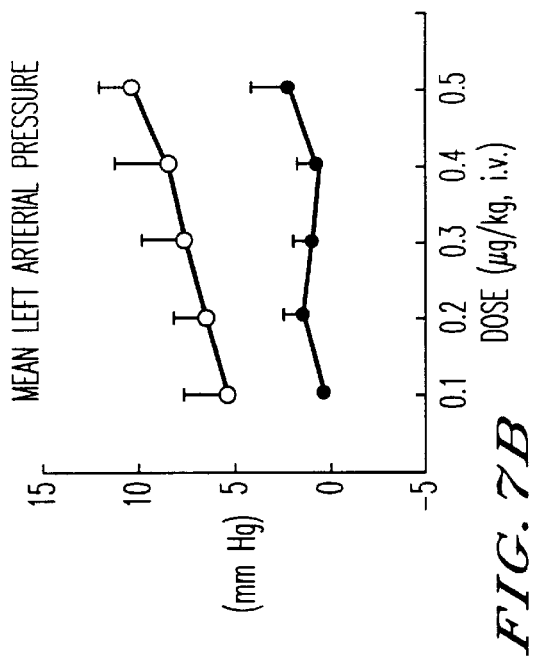
Figure 7B:
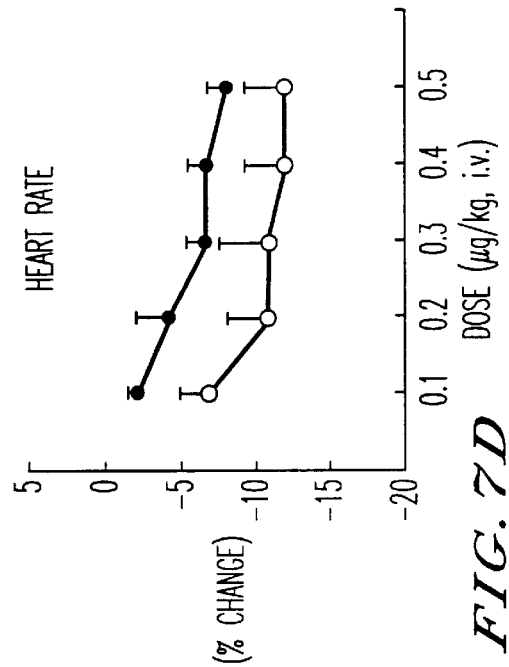
Figure 7C:
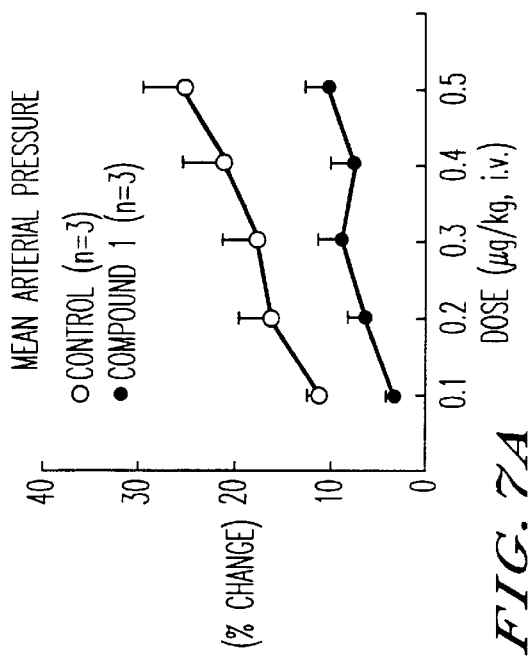
Figure 7D:
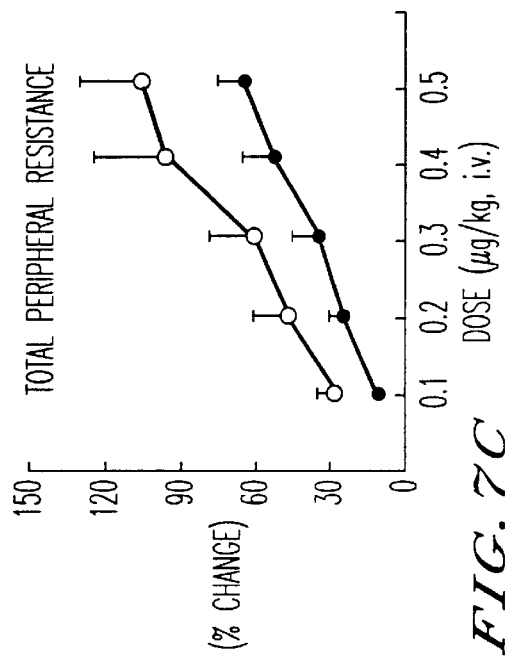

FIG. 5 compares the effects of intravenous administration of Compound 1 (0.5 mg/kg) and Compound 2 (enalaprilat) (1 mg/kg or 4 mg/kg) on total peripheral resistance in conscious pigs with heart failure. While the effects were not dose-dependent, suggesting maximal effect, both doses of Compound 2 did significantly reduce the total peripheral resistance to a similar level throughout 90-minute observation period. The reduction in total peripheral resistance by administration of Compound 1 (0.5 mg/kg) was greater than that induced by either dose of Compound 2. FIG. 6 compares the changes in mean arterial pressure, LV dP/dt. cardiac output and total peripheral resistance at 60 minutes after administration of Compound 1 or Compound 2.

Step E: Effects of ET-1 in the Absence and Presence of Compound 1 in Heart Failure FIG. 7 shows the effects of cumulative intravenous bolus injections of ET-1 (total dose of 0.5 μg/kg) on mean arterial pressure, mean left atrial pressure, total peripheral resistance and heart rate before and after intravenous administration of Compound 1 at a dose of 0.5 mg/kg. ET-1 induced significant dose-dependent increases in mean arterial pressure, mean left atrial pressure and total peripheral resistance. Heart rate decreased, but not dose-dependently. The hemodynamic responses to ET-1 were markedly attenuated after administration of Compound 1, suggesting the 0.5 mg/kg, i.v. dose of Compound 1 to be capable of significant blocking the effects of exogenous ET-1.

Compound 1, at a dose of 0.5 mg/kg, i.v. reduced the elevated vascular resistance but did not affect myocardial contractility in conscious pigs with heart failure. This acute effect of Compound 1 was greater than that of 1 mg/kg or 4 mg/kg, i.v. Compound 2. The salutary effects of Compound 1 in this heart failure model were attributed to ET receptor antagonism since the hemodynamic responses to an ET-1 challenge were markedly attenuated by the same dose of Compound 1.

What is claimed is:

1. A pharmaceutical composition for preventing or treating heart failure, which comprises an endothelin antagonist of the formula (I) or a pharmaceutically acceptable salt thereof, and a pharmaceutically acceptable carrier:

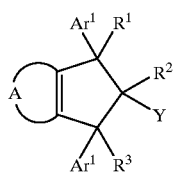

(I)

wherein:

each of $Ar^1$ and $Ar^2$ is independently phenyl or thienyl, which are each optionally substituted by 1 to 4 groups selected from the group consisting of halogen, hydroxyl, amino, carboxyl, $C_1$–$C_6$ alkoxycarbonyl, mono- or di-$C_1$–$C_6$ alkylaminocarbonyl, carbamoyl, tetrazol-5-yl, methylenedioxy, $C_1$–$C_6$ alkoxy, $C_2$–$C_6$ alkenyloxy, mono- or di-$C_1$–$C_6$ alkylamino, $C_1$–$C_6$ alkyl, $C_2$–$C_6$ alkenyl and $C_2$–$C_6$ alkynyl, wherein the $C_1$–$C_6$alkoxy, $C_2$–$C_6$ alkenyloxy, mono- or di-$C_1$–$C_6$ alkylamino, $C_1$–$C_6$ alkyl, $C_2$–$C_6$ alkenyl and $C_2$–$C_6$ alkynyl are each optionally substituted by 1 to 3 groups which are selected from the group consisting of phenyl, pyridyl, imidazolyl, hydroxyl, $C_1$–$C_6$ alkoxy, amino, mono- or di-$C_1$–$C_6$ alkylamino, hydroxy $C_1$–$C_6$ alkylcarbonyl, $C_1$–$C_6$ acyloxy $C_1$–$C_6$ alkylcarbonyl, carboxy $C_1$–$C_6$ alkoxycarbonyl, carboxy $C_1$–$C_6$ alkoxycarbonyl $C_1$–$C_6$ alkoxycarbonyl, $C_1$–$C_6$ alkoxycarbonyl, mono- or di-$C_1$–$C_6$ alkylaminocarbonyl, carbamoyl, $C_1$–$C_6$ alkylsulfonylaminocarbonyl, tetrazol-5-yl-amino carbonyl, carboxyl, $SO_3H$, $PO_3H_2$, tetrazol-5-yl, 2-oxo-3H-1,2,3,5-oxathiadiazol-4-yl and 5-oxo-4H-1,2,4-oxadiazol-3-yl; and wherein when hydroxyl and carboxyl are selected as substituents, they optionally together form a lactone ring;

each of $R^1$, $R^2$ and $R^3$ is independently hydrogen, hydroxyl or $C_1$–$C_6$ alkyl, or $R^1$ and $R^2$, or $R^2$ and $R^3$ together form a single bond;

Y is —CO—$R^4$, wherein $R^4$ is a hydroxyl, amino, a $C_1$–$C_6$ alkoxy, mono- or di-$C_1$–$C_6$ alkylamino, $C_1$–$C_6$ alkylsulfonylamino, or arylsulfonylamino or aryl $C_1$–$C_6$ alkylsulfonylamino, wherein hydrogen atom(s) on the aryl ring thereof are optionally replaced by $C_1$–$C_6$ alkyl, $SO_3H$, $PO_3H_2$, tetrazol-5-yl, 2-oxo-3H-1,2,3,5-oxathiadiazol-4-yl or 5-oxo-4H-1,2,4-oxadiazol-3-yl; and A is a group which forms together with the adjacent carbon-carbon double bond a 5- or 6-membered heteroaromatic ring including 1 to 4 hetero atoms selected from the group consisting of nitrogen, oxygen and sulfur, wherein 1 or 2 hydrogen atoms on the heteroaromatic ring are optionally replaced with hydroxyl, amino, $C_1$–$C_6$ alkoxy, $C_1$–$C_6$ alkylthio, halogen, cyano, nitro, mono- or di-$C_1$–$C_6$ alkylamino which are optionally substituted by hydroxyl at the alkyl moiety, $C_3$–$C_8$ cycloalkylamino which is optionally substituted by hydroxyl at the alkyl or alkylene moiety, $C_3$–$C_8$ cycloalkyl $C_1$–$C_6$ alkylamino which is optionally substituted by hydroxyl at the alkyl or alkylene moiety, N-($C_1$–$C_6$ alkyl)-N-($C_3$–$C_8$ cycloalkyl) amino which is optionally substituted by hydroxyl at the alkyl or alkylene moiety, N-($C_1$–$C_6$ alkyl)-N-(aroyl) amino which is optionally substituted by hydroxyl at the alkyl moiety, $C_4$–$C_7$ cyclic imino which is optionally substituted by hydroxyl, the alkylene moiety, carboxyl, $C_1$–$C_6$ alkoxycarbonyl, formyl, $C_2$–$C_6$ alkanoyl, aroyl, or $C_1$–$C_6$alkyl, $C_3$–$C_8$ cycloalkyl, $C_3$–$C_8$ cycloalkyl $C_1$–$C_6$ alkyl, $C_2$–$C_6$ alkenyl or $C_2$–$C_6$ alkynyl, which are each optionally substituted by 1 to 3 substituents selected from the group consisting of hydroxyl, amino, $C_1$–$C_6$ alkoxy and mono- or di-$C_1$–$C_6$ alkylamino, and wherein when the heteroaromatic ring includes one or more nitrogen atoms, the nitrogen atom(s) are optionally oxidized to form an N-oxide group.

2. The composition of claim 1, wherein A is a group which forms together with the adjacent carbon-carbon double bond a 5- or 6-membered nitrogen-containing aromatic ring or the corresponding N-oxide ring, thereof, wherein 1 or 2 hydrogen atoms on the heteroaromatic ring are optionally replaced with hydroxyl, amino, $C_1$–$C_6$ alkoxy, $C_1$–$C_6$ alkylthio, mono- or di-$C_1$–$C_6$ alkylamino which are each optionally substituted by hydroxyl at the alkyl moiety, $C_3$–$C_8$ cycloalkylamino which is optionally substituted by hydroxyl at the alkyl or alkylene moiety, $C_3$–$C_8$ cycloalkyl $C_1$–$C_6$ alkylamino which is optionally substituted by hydroxyl at the alkyl or alkylene moiety, N-($C_1$–$C_6$ alkyl-N-($C_3$–$C_8$ cycloalkyl)amino which is optionally substituted by hydroxyl at the alkyl or alkylene moiety, N-$C_1$–$C_6$ alkyl-N-(aroyl)amino which is optionally substituted by hydroxyl at the alkyl moiety, $C_4$–$C_7$ cyclic imino which is optionally substituted by hydroxyl at the alkylene moiety, or $C_1$–$C_6$ alkyl, $C_3$–$C_8$ cycloalkyl, $C_3$–$C_8$ cycloalkyl $C_1$–$C_6$ alkyl, $C_2$–$C_6$ alkenyl or $C_2$–$C_6$ alkynyl, which are each optionally substituted by 1 to 3 groups selected from the group consisting of hydroxyl, amino, $C_1$–$C_6$ alkoxy and mono- or di-$C_1$–$C_6$ alkylamino.

3. The composition of claim 2, wherein A is a group which forms together with the adjacent carbon-carbon double bond a pyridine, pyrimidine, pyridazine, pyrazine or thiazole ring.

4. The composition of claim 3, wherein A is a group which forms together with the adjacent carbon-carbon double bond a pyridine ring.

5. The composition of claim 1, wherein the endothelin antagonist is selected from the group consisting of 6-ethoxycarbonyl-5-(3,4-methylene-dioxyphenyl)-7-(4-methoxyphenyl)cyclopenteno(1,2-b)pyridine, (5RS,6SR,7SR)-6-carboxy-5-(3,4-methylenedioxyphenyl)-7-(4-methoxyphenyl) cyclopenteno(1,2-b) pyridine, 6-ethoxycarbonyl-5,7-diphenylcyclopenteno-(1,2-b) pyridine, (5RS,6SR,7SR)-6-carboxy-5,7-diphenylcyclopenteno(1,2-b)pyridine, 6-ethoxycarbonyl-5,7-di(4-methoxyphenyl)cyclopenteno (1,2-b)pyridine, (5RS,6SR,7SR)-6-carboxy-5,7-di(4-methoxyphenyl) cyclopenteno(1,2-b)pyridine, 6-ethoxycarbonyl-5,7-di (3,4-methylenedioxyphenyl)cyclopenteno(1,2-b) pyridine, (5RS,6SR,7SR)-6-Carboxy-5,7-di(3,4-methylenedioxyphenyl)cyclopenteno(1,2-b)pyridine, 6-ethoxycarbonyl-7-(3,4-methylenedioxyphenyl)-5-(4-methoxyphenyl)-7-(3,4-methylenedioxyphenyl) cyclopenteno(1,2-b)pyridine, (5RS,6SR,7SR)-6-carboxy-7-(3,4-methylenedioxyphenyl)-5-(4-methoxyphenyl)cyclopenteno(1,2-b)pyridine, 6-ethoxycarbonyl-5-phenyl-7-(4-methoxyphenyl) cyclopenteno(1,2-b)pyridine, (5RS,6SR,7SR)-6-carboxy-5-phenyl-7-(4-methoxyphenyl)cyclopenteno (1,2-b)pyridine, 6-ethoxycarbonyl-7-phenyl-5-(4-methoxyphenyl)cyclopenteno(1,2-b)pyridine, (5RS, 6SR,7SR)-6-carboxy-7-phenyl-5-(4-methoxyphenyl) cyclopenteno(1,2-b)pyridine, 6-ethoxycarbonyl-5-phenyl-7-(3,4-methylenedioxyphenyl)cyclopenteno(1, 2-b)pyridine, (SRS,6SR,7SR)-6-carboxy-5-phenyl-7-(3,4-methylenedioxyphenyl)cyclopenteno(1,2-b) pyridine, 6-ethoxycarbonyl-7-phenyl-5-(3,4-methylenedioxyphenyl)cyclopenteno(1,2-b)pyridine, (5RS,6SR,7SR)-6-carboxy-7-phenyl-5-(3,4-methylenedioxyphenyl) cyclopenteno(1,2-b)pyridine, (5RS,6SR,7SR)-6-carboxy-7-(3,4-methylenedioxyphenyl)-5-(4-ethoxyphenyl) cyclopenteno(1,2-c)pyridine, (5RS,6SR,7SR)-6-carboxy-5-(3,4-methylenedioxyphenyl)-7-(4-methoxyphenyl)cyclopenteno-(1,2-c)pyridine, (5RS,6SR,7SR)-6-carboxy-2-propoxy-5-(3,4-methylenedioxyphenyl)-7-(4-methoxyphenyl) cyclopenteno(1,2-b)-pyridine, (5RS,6S,7SR)-6-carboxy-2-methyl-5-(3,4-methylenedioxyphenyl)-7-(4-methoxyphenyl)cyclopenteno(1,2-b)-pyridine, (SRS,6SR,7SR)-2-butyl-6-carboxy-5-(3,4-methylenedioxyphenyl)-7-(4-methoxyphenyl) cyclopenteno(1,2-b)pyridine, (5RS,6SR,7SR)-6-carboxy-2-ethylaminomethyl-5-(3,4-methylenedioxyphenyl)-7-(4-methoxyphenyl) cyclopenteno(1,2-b)pyridine, (SRS,6SR,7SR)-6-carboxy-5-(3,4-methylenedioxyphenyl )-7-(4-methoxyphenyl)cyclopenteno-(1,2-b)pyridine, N-oxide (SRS,6SR,7SR)-6-carbamoyl-5-(3,4-methylenedioxyphenyl)-7-(4-methoxyphenyl)-cyclopenteno(1,2-b)pyridine, (5RS,6SR,7SR)-6-methanesulfonylaminocarbonyl-5-(3,4-methylenedioxyphenyl)-7-(4-methoxyphenyl) cyclopenteno(1,2-b)pyridine, (SRS,6SR,7SR)-6-(4-isopropylbenzenesulfonylaminocarbonyl)-5-(3,4-methylenedioxyphenyl)-7-(4-methoxyphenyl) cyclopenteno (1,2-b)pyridine, 6-carboxy-5-hydroxy-5-(3,4-methylenedioxyphenyl)-7-(4-methoxyphenyl) cyclopent-1,4-dieno(1,2-b)pyridine, (5RS,6SR,7SR)-6-carboxy-7-(2-carboxymethoxy-4-methoxyphenyl)-5-(3,4-methylenedioxyphenyl)cyclopenteno(1,2-b) pyridine, (5RS,6SR,7RS)-6-carboxy-5-(2-carboxymethoxy-4-methoxyphenyl)-7-(3,4-methylenedioxyphenyl)cyclopenteno(1,2-c)pyridine, (5RS,6SR,7SR)-6-carboxy-7-(2-hydroxy-4-methoxyphenyl)-5-(3,4-methylenedioxyphenyl) cyclopenteno(1,2-b)pyridine, (5RS,6SR,7SR)-6-carboxy-7-(2-(2-hydroxyethoxy)-4-methoxyphenyl)-5-(3,4-methylene dioxyphenyl)cyclopenteno(1,2-b) pyridine, (5RS,6SR,7SR)-6-carboxy-7-(2-(2-methylaminoethoxy)-4-methoxyphenyl)-5-(3,4-methylenedioxyphenyl)s cyclo-penteno(1,2-6) pyridine, (SRS,6SR,7SR)-6-carboxy-2-ethoxymethyl-7-(4-methoxyphenyl)-5-(3,4-methylenedioxyphenyl) cyclopenteno(1,2-b)pyridine, (5RS,6SR,7SR)-6- carboxy-7-(4-methoxyphenyl)-5-(3,4-methylenedioxyphenyl)-2-propylcyclopenteno-(1,2-b)pyridine, (5RS,6SR,7SR)-6-carboxy-2-isobutyl-7-(4-methoxyphenyl)-5-(3,4-methylenedioxyphenyl)cyclopenteno-(1,2-b)pyridine, 6-carboxy-7-hydroxy-7-(4-methoxyphenyl)-5-(3,4-methylenedioxyphenyl)cyclopent-1,3-dieno(1,2-b)pyridine, 6-carboxy-5-hydroxy-7-(4-methoxyphenyl)-5-(3,4-methylenedioxyphenyl)-2-propylcyclopent-1,3-dieno-(2,1-b)pyridine, (5RS,6SR,7RS)-6-carboxy-5-hydroxy-7-(4-methoxyphenyl)-5-(3,4-methylenedioxyphenyl)-cyclopenteno(1,2-b)-pyridine, (5RS,6SR,7SR)-6-carboxy-7-(4-hydroxyphenyl)5-(3,4-methylenedioxyphenyl)-cyclopenteno(1,2-b)pyridine, (5RS,6SR,7RS)-6-carboxy-7-(4-(2-hydroxyethoxy)phenyl)-5-(3,4-methylenedioxyphenyl)cyclopenteno(1,2-b)-pyridine, (5RS,6SR,7SR)-6-carboxy-7-(4-(2-methylaminoethoxy)phenyl)-5-(3,4-methylenedioxyphenyl)-cyclopenteno(1,2-b)-pyridine, (5RS,6SR,7SR)-6-carboxy-7-(4-hydroxymethylphenyl)-5-(3,4-methylenedioxyphenyl)cyclopenteno-(1,2-b)pyridine, (5RS,6SR,7SR)-6-carboxy-5-(3,4-methylenedioxyphenyl)-7-(3-thienyl)cyclopenteno(1,2-b)pyridine, (5RS,6SR,7RS)-7-(4-methoxyphenyl)-5-(3,4-methylenedioxyphenyl)-6-(2-oxo-3H-1,2,3,5-oxathiadiazol-4-yl)cyclopenteno(1,2-b)pyridine, (5RS,6SR,7SR)-6-(5-oxo-4H-1,2,4-oxediazol-3-yl)-5-(3,4-methylenedioxyphenyl)-7-(4-methoxyphenyl)cyclopenteno(1,2-b)pyridine, (5RS,6SR,7SR)-6-(tetrazol-5-yl)-5-(3,4-methylenedioxyphenyl)-7-(4-methoxyphenyl)cyclopenteno(1,2-b)pyridine, (5RS,6SR,7SR)-5-(3,4-methylenedioxyphenyl)-6-methoxycarbonyl-7-(4-methoxyphenyl)cyclopenteno(1,2-b)pyridine, (5RS,6SR,7SR)-7-(2-ethoxycarbonylmethoxy-4-methoxyphenyl)-6-carboxy-5-(3,4-methylenedioxyphenyl)cyclopenteno(1,2-b)pyridine, (5RS,6SR,7SR)-6-carboxy-7-(2-(tetrazol-5-ylaminocarbonylmethoxy)-4-methoxyphenyl)-5-(3,4-methylendioxyphenyl)cyclopenteno(1,2-b)pyrldine, (5RS,6SR,7SR)-7-(2-carbamoylmethoxy-4-methoxyphenyl)-6-carboxy-5-(3,4-methylendioxyphenyl)cyclopenteno(1,2-b)pyridine, (5RS,6SR,7SR)-6-carboxy-7-(2-methanesulfonylaminocarbonylmethoxy-4-methoxyphenyl)-5-(3,4-methylenedioxyphenyl)cyclopenteno(1,2-b)pyridine, (5RS,6SR,7SR)-6-carboxy-7-(2-(tetrazol-5-ylmethoxy)-4-methoxyphenyl)-5-(3,4-methylenedioxyphenyl)cyclopenteno(1,2-b)pyridine, (5RS,6SR,7SR)-6-carboxy-7-(2-(1-methoxycarbonylpropoxy)-4-methoxyphenyl)-5-(3,4-methylenedioxyphenyl)cyclopenteno(1,2-b)pyridine, (5RS,6SR,7SR)-6-carboxy-7-(2-(1-methoxycarbonylpropoxy)-4-methoxyphenyl)-5-(3,4-methylenedioxyphenyl)cyclopenteno(1,2-b)pyridine, (5RS,6SR,7SR)-6-carboxy-7-(2-(1-carboxypropoxy)-4-methoxyphenyl)-5-(3,4-methylenedioxyphenyl)cyclopenteno(1,2-b)pyridine, (5RS,6SR,7SR)-6-carboxy-7-(2-(1-carboxypropoxy)-4-methoxyphenyl)-5-(3,4-methylendioxyphenyl)penteno(1,2-b)pyridine, (5RS,6SR,7SR)-7-(2-(1-ethoxycarbonylethoxy)-4-methoxyphenyl)-6-carboxy-5-(3,4-methylenedioxyphenyl)cyclopenteno(1,2-b)pyridine, (5RS,6SR,7SR)-6-carboxy-7-(2-(1-carboxyethoxy)-4-methoxyphenyl)-5-(3,4-methylenedioxyphenyl)cyclopenteno(1,2-b)pyridine, (5RS,6SR,7SR)-6-carboxy-7-(2-(2-carboxyethoxy)-4-methoxyphenyl)-5-(3,4-methylenedioxyphenyl)penteno(1,2-b)pyridine, (5RS,6SR,7SR)-6-carboxy-7-(2-(2-(2-carboxyethoxycarbonyl)ethoxy)-4-methoxyphenyl)-5-(3,4-methylenedioxyphenyl)cyclopenteno(1,2-b)pyridine, (5RS,6SR,7SR)-6-carboxy-7-(2-(2-(2-(2-carboxyethoxycarbonyl)ethoxycarbonyl)ethoxy)-4-methoxyphenyl)-5-(3,4-methylenedioxyphenyl)cyclopenteno(1,2-b)pyridine, (5RS,6SR,7SR)-6-carboxy-7-(2-(2-benzyloxy-1-methoxycarbonylethoxy)-4-methoxyphenyl)-5-(3,4-methylenedioxyphenyl)cyclopenteno(1,2-b)pyridine, (5RS,6SR,7SR)-6-carboxy-7-(2-(1-methoxycarbonylethenyloxy)-4-ethoxyphenyl)-5-(3,4-methylenedioxyphenyl)cyclopenteno(1,2-b)pyridine, (5RS,6SR,7SR)-6-carboxy-7-(2-(2-hydroxy-1-methoxycarbonylethoxy)-4-methoxyphenyl)-5-(3,4-methylenedioxyphenyl)cyclopenteno(1,2-b)pyridine, (5RS,6SR,7SR)-6-carboxy-7-(2-(1-carboxy-2-hydroxyethoxy)-4-methoxyphenyl)-5-(3,4-methylenedioxyphenyl)cyclopenteno (1,2-b)pyridine, (5RS,6SR,7SR)-6-carboxy-7-(2-(1-carboxyethenyloxy)-4-methoxyphenyl)-5-(3,4-methylenedioxyphenyl)cyclopenteno(1,2-b)pyridine, (5RS,6SR,7SR)-6-carboxy-2-hydroxymethyl-5-(3,4-methylenedioxyphenyl)-7-(4-methoxyphenyl)cyclopenteno(1,2-b)pyridine, (5RS,6SR,7SR)-2-ethoxymethyl-6-carboxy-7-(2-carboxymethoxy-4-methoxyphenyl)-5-(3,4-methylenedioxyphenyl)cyclopenteno(1,2-b)pyridine, (5RS,6SR,7SR)-7-(2-ethylaminocarbonylmethoxy-4-methoxyphenyl)-2-ethylaminomethyl-6-carboxy-5-(3,4-methylenedioxyphenyl)cyclopenteno(1,2-b)pyridine, (5RS,6SR,7SR)-2-ethylaminomethyl-6-carboxy-7-(2-carboxymethoxy-4-methoxyphenyl)-5-(3,4-methylenedioxyphenyl)cyclopenteno(1,2-b)pyridine, (5RS,6SR,7SR)-6-carboxy-7-(2-carboxylmethoxy-4-methoxyphenyl)-2-propoxy-5-(3,4-methylenedioxyphenyl)cyclopenteno(1,2-b)pyridine, (5RS,6SR,7SR)-2-ethyl-6-carboxy-5-(3,4-methylenedioxyphenyl)-7-(4-methoxyphenyl)cyclopenteno(1,2-b)pyridine, (5RS,6SR,7SR)-6-carboxy-2-cyclopropyl-5-(3,4-methylenedioxyphenyl)-7-(4-methoxyphenyl)cyclopenteno(1,2-b)pyridine, (5RS,6SR,7SR)-6-carboxy-2-pentyl-5-(3,4-methylenedioxyphenyl)-7-(4-methoxyphenyl)cyclopenteno(1,2-b)pyridine, 6-carboxy-5-hydroxy-2-(3-butenyl)-5-(3,4-methylenedioxyphenyl)-7-(4-methoxyphenyl)cyclopent-1,3-dieno(2,1-b)pyridine, (5RS,6SR,7SR)-6-carboxy-2-(3-butenyl)-5-(3,4-methylenedioxyphenyl)-7-(4-methoxyphenyl)cyclopenteno(1,2-b)pyridine, (5RS,6SR,7SR)-6-carboxy-2-propylthio-5-(3,4-methylenedioxyphenyl)-7-(4-methoxyphenyl), penteno(1,2-b)pyridine, (5RS,6SR,7SR)-6-carboxy-2-propylamino-5-(3,4-methylenedioxyphenyl)-7-(4-methoxyphenyl)penteno(1,2-b)pyridine, (5RS,6SR,7SR)-6-carboxy-2-piperidino-5-(3,4-methylenedioxyphenyl)-7-(4-methoxyphenyl)penteno(1,2-b)pyridine, (5RS,6SR,7SR)-6-carboxy-7-(2-carboxymethoxy-4-methoxyphenyl)-2-butyl-5-(3,4-methylenedioxyphenyl)cyclopenteno(1,2-b)pyridine, (SRS,6SR,7SR)-6-carboxy-7-(2-carboxymethoxy-4-methoxyphenyl)-2-propylamino-5-(3,4-methylenedioxyphenyl)cyclopenteno(1,2-b)pyridine, (5RS,6SR,7SR)-5-carboxy-7-(2-carboxymethylamino-4-methoxyphenyl)-5-(3,4-methylenedioxyphenyl) cyclopenteno(1,2-b)pyridine, (5RS,7SR)-6-ethoxycarbonyl-7-(2-carboxymethylamino-4-methoxyphenyl)-5-(3,4-methylenedioxyphenyl) cyclopenteno(1,2-b)pyridine, (SRS,6SR,7SR)-6-carboxy-7-(2-pyridyl)-5-(3,4-methylenedioxyphenyl) cyclopenteno(1,2-b)pyridine, (SRS,6SR,7SR)-6-carboxy-5-(3-fluorophenyl)-7-(4-methoxyphenyl)cyclopenteno(1,2-b)pyridine, (SRS,6SR,7SR)-6-carboxy-5-(3-methoxyphenyl)-7-(4-methoxyphenyl) cyclopenteno(1,2-b)pyridine, (5RS,6SR,7SR)-6-carboxy-7-(4-fluorophenyl)-5-(3,4-methylenedioxyphenyl)cyclopenteno(1,2-b)pyridine, (5RS,6SR,7SR)-6-carboxy-5-(2-methoxyphenyl)-7-(4-methoxyphenyl)cyclopenteno(1,2-b)pyridine, (SRS,6SR,7SR)-7-(2-(5-oxo-4H-1,2,4-oxadiazol-3-ylmethoxy)-4-methoxyphenyl)-6-carboxy-5-(3,4-methylene-dioxyphenyl)cyclopenteno(1,2-b)pyridine, 6-carboxy-5-hydroxy-5-(3,4-methylene-dioxyphenyl)-7-(4-methexyphenyl)cyclopent-1,3-dieno(2,1-d) pyrimidine 6-carboxy-5-hydroxy-2-butyl-5-(3,4-methylenedioxyphenyl)-7-(methoxyphenyl)cyclopent-1,3-dieno(2,1-d)pyrimidine (5RS,6SR,7SR)-6-carboxy-7-(2-(1-carboxypentyloxy)-4-methoxyphenyl)-5-(3,4-methylenedioxyphenyl) cyclopenteno(1,2-b)pyridine, (5RS,6SR,7SR)-6-carboxy-7-(2-((E)-2-carboxyethenyl)-4-methoxyphenyl)-5-(3,4-methylenedioxyphenyl) cyclopenteno(1,2-b)pyridine, (SRS,6SR,7SR)-6-carboxy-5-(3,4-methylenedioxyphenyl)-7-(2-(2-methoxycarbonylethyl)-4-methoxyphenyl) cyclopenteno(1,2-b)pyridine, (5RS,6SR,7SR)-6-Carboxy-7-(2-(2-carboxyethyl)-4-methoxyphenyl)-5-(3,4-methylenedioxyphenyl)cyclopenteno(1,2-b) pyridine, (SRS,6SR,7SR)-6-carboxy-5-(3,4-methylenedioxyphenyl)-7-(2-(2-methoxycarbonylpropyl)-4-methoxyphenyl) cyclopenteno(1,2-b)pyridine, (5RS,6SR,7SR)-6-carboxy-7-(2-(2-carboxypropyl)-4-methoxyphenyl)-5-(3,4-methylenedioxyphenyl)penteno(1,2-b)pyridine, (SRS,6SR,7SR)-6-carboxy-5-(3,4-methylenedioxyphenyl)-7-(2-(2-carboxy-2-propenyl)-4-methoxyphenyl)cyclopenteno(1,2-b)pyridine, (5RS,6SR,7SR)-6-carboxy-7-(2-(2-carboxy-2-propenyl)-4-methoxyphenyl)-5-(3,4-methylenedioxyphenyl) cyclopenteno(1,2-b)pyridine, (SRS,6SR,7SR)-6-carboxy-7-(2-(1,2-dihydroxy-2-methoxycarbonylethyl)-4-methoxyphenyl)-5-(3,4-methylenedioxyphenyl)cyclopenteno(1,2-b)pyridine, (SRS,6SR,7SR)-6-carboxy-7-(2-(2-carboxy-1,2-dihydroxyethyl)-4-methoxyphenyl)-5-(3,4-methylenedioxyphenyl)cyclopenteno(1,2-b)pyridine, (5RS,6SR,7SR)-6-carboxy-7-(2-(3-hydroxy-1-propynyl)-4-methoxyphenyl)-5-(3,4-methylenedioxyphenyl)cyclopenteno(1,2-b)pyridine, (5RS,6SR,7SR)-6-carboxy-7-(2-((Z)-(3-hydroxy-1-propenyl)-4-methoxyphenyl)-5-(3,4-methylenedioxyphenyl)cyclopenteno(1,2-b)pyridine, (5RS,6SR,7SR)-6-carboxy-7-(2-((E)-(3-hydroxy-1-propenyl))-4-methoxyphenyl)-5-(3,4-methylenedioxyphenyl)cyclopenteno(1,2-b)pyridine, (5RS,6SR,7SR)-6-carboxy-7-(2-(3-hydroxypropyl)-4-methoxyphenyl)-5-(3,4-methylenedioxyphenyl) cyclopenteno(1,2-b)pyridine, (SRS,6SR,7SR)-6-carboxy-7-(2-(1,2-dihydroxyethyl)-4-methoxyphenyl)-5-(3,4-methylenedioxyphenyl)cyclopenteno(1,2-b) pyridine, (SRS,6SR,7SR)-6-carboxy-7-(2-(1,3-dihydroxypropyl)-4-methoxypheny)-5-(3,4-methylenedioxyphenyl)cyclopenteno(1,2-b)pyridine, (SRS,6SR,7SR)-6-carboxy-7-(2-(2,3-dihydroxypropyl)-4-methoxypheny)-5-(3,4-methylenedioxyphenyl)cyclopenteno(1,2-b)pyridine, (5RS,6SR,7SR)-6-carboxy-7-(2-(1,2,3-trihydroxypropyl)-4-methoxypheny)-5-(3,4-methylenedioxyphenyl)cyclopenteno(1,2-b)pyridine, (5RS,6SR,7SR)-6-carboxy-7-(2-(1,2,3-trihydroxypropyl)-4-methoxypheny)-5-(3,4-methylenedioxyphenyl)cyclopenteno(1,2-b)pyridine, (SRS,6SR,7SR)-6-carboxy-7-(2-(1-carboxy-2-hydroxyethoxy)-4-methoxyphenyl)-2-propylamino-5-(3,4-methylene-dioxyphenyl)cyclopenteno(1,2-b) pyridine, (SRS,6SR,7SR)-6-carboxy-7-(2-(1-carboxyethenyloxy)-4-methoxyphenyl)-2-propylamino-5-(3,4-methylenedioxyphenyl) cyclopenteno(1,2-b)pyridine, (SRS,6SR,7SR)-7-(2-ethoxycarbonylmethoxy-4-methoxyphenyl)-6-carboxy-2-(N-propyl-N-methylamino)-5-(3,4-methylenedioxyphenyl)cyclopenteno(1,2-b)pyridine, (5RS,6SR,7SR)-6-carboxy-7-(2-carboxymethoxy-4-methoxyphenyl)-2-(N-propyl-N-methylamino)-5-(3,4-methylenedioxyphenyl)cyclopenteno(1,2-b)pyridine, (SRS,6SR,7SR)-6-carboxy-7-(2-carboxymethoxy-4-methoxyphenyl)-2-methylamino-5-(3,4-methylenedioxyphenyl)cyclopenteno(1,2-b)pyridine, (SRS,6SR,7SR)-6-carboxy-7-(2-carboxymethoxy-4-methoxyphenyl)-2-(N,N-dimethylamino)-5-(3,4-methylenedioxyphenyl)cyclopenteno(1,2-b)pyridine, (5RS,6SR,7SR)-6-carboxy-7-(2-carboxymethoxy-5-tert-butyl-4-methoxyphenyl)-2-methylamino-5-(3,4-methylenedioxyphenyl)cyclopenteno(1,2-b)pyridine, (SRS,6SR,7SR)-2-amino-6-carboxy-7-(2-carboxymethoxy-4-methoxyphenyl)-5-(3,4-methylenedioxyphenyl)cyclopenteno(1,2-b)pyridine, (SRS,6SR,7SR)-6-carboxy-7-(2-carboxymethoxy-4-methoxyphenyl)-2-((N-benzoyl)-3-hydroxypropylamino)-5(3,4-methylenedioxyphenyl) cyclopenteno(1,2-b)pyridine, (SRS,6SR,7SR)-6-Carboxy-7-(2-carboxymethoxy-4-methoxyphenyl)-2-(3-hydroxypropylamino)-5-(3,4-methylene-dioxyphenyl)cyclopenteno(1,2-b)pyridine, (SRS,6SR,7SR)-6-carboxy-7-(2-carboxymethoxy-4-methoxyphenyl)-2-(2-hydroxyethylamino)-5-(3,4-methylenedioxyphenyl)cyclopenteno(1,2-b)pyridine, (SRS,6SR,7SR)-6-carboxy-5-(3,5-dimethoxyphenyl) 7-(4-methoxypheny)cyclopenteno(1,2-b)pyridine, (5RS,6SR,7SR)-6-carboxy-2-(3-propoxy-5-methoxyphenyl)-7-(4-methoxyphenyl)cyclopenteno-(1,2-b)pyridine, (5RS,6SR,7SR)-6-carboxy-5-(3,4-methylenedioxy-5-methoxyphenyl)-7-(4-methoxyphenyl)cyclopenteno(1,2-b)pyridine, (5RS,6SR,7SR)-6-carboxy-5-(3-benzyloxy-4-methoxyphenyl)-7-(4-methoxyphenyl)cyclopenteno(1,2-b) pyridine, (5RS,6SR,7SR)-6-carboxy-5-(3-hydroxy-4-methoxyphenyl)-7-(4-methoxypheny)cyclopenteno-(1,2-b)pyridine, (5RS,6SR,7SR)-5-(4-Indolyl)-6-carboxy-7-(4-methoxyphenyl)cyclopenteno(1,2-b) pyridine, (SRS,6SR,7SR)-7-(5-Indolyl)-6-carboxy-5-(3,4-methylenedioxyphenyl)cyclopenteno(1,2-b) pyridine, (5RS,6SR,7SR)-7-(4-rthoxyphenyl)-6-carboxy-5-(3,4-methylenedioxyphenyl)cyclopenteno (1,2-b)pyridine, (5RS,6SR,7SR)-7-(2-(4-imidazolylmethoxy)-4-methoxyphenyl)-6-carboxy-5-(3,4-methylenedioxyphenyl)cyclopenteno(1,2-b)

pyridine, (5RS,6SR,7SR)-7-(2-(2-oxo-4,5-dihydrofuryloxy)-4-methoxyphenyl)-6-carboxy-5-(3,4-methylenedioxyphenyl)cyclopenteno(1,2-b)pyridine, (5RS,6SR,7SR)-6-carboxy-7-(2-(1-carboxy-3-hydroxypropoxy)-4-methoxyphenyl)-5-(3,4-methylenedioxyphenyl)cyclopenteno(1,2-b)pyridine, (5RS,6SR,7SR)-7-(2-acetoxymethylcarbonylmethoxy-4-methoxyphenyl-6-carboxy-5-(3,4-methylenedioxyphenyl)cyclopenteno(1,2-b)pyridine, (5RS,6SR,7SR)-2-isopropylamino-6-carboxy-5-(3,4-methylenedioxyphenyl-7-(4-methoxyphenyl)cyclopenteno(1,2-b)pyridine, 6-carboxy-5-(3,4-methylenedioxyphenyl-7-(4-methoxyphenyl)cyclopent-1,2-dieno(1,2-b)pyridine, 6-carboxy-5-(3,4-methylenedioxyphenyl-7-(4-methoxyphenyl)cyclopent-1,2-dieno(2,1-b)pyridine, (5RS,6SR,7SR)-6-carboxy-2,7-dimethyl-5-(3,4-methylenedioxyphenyl-7-(4-methoxyphenyl)cyclopenteno(1,2-b)pyridine, (5RS,6SR,7SR)-6-carboxy-2-pyrrolidino-5-(3,4-methylenedioxyphenyl-7-(4-methoxyphenyl)cyclopenteno(1,2-b)pyridine, (5RS,6SR,7SR)-6-carboxy-7-(2,3-dibydro-5-benzofuranyl)-5-(3,4-methylenedioxyphenyl)cyclopenteno(1,2-b)pyridine, (5RS,6SR,7SR)-6-carboxy-7-(2-(2-hydroxyethoxy)-4-methoxyphenyl)-2-(N-methyl-3-hydroxypropylamino)-5-(3,4-methylenedioxyphenyl)cyclopenteno(1,2-b)pyridine, (5RS,6SR,7SR)-6-carboxy-2-cyclopropylamino-5-(3,4-methylenedioxyphenyl)-7-(4-methoxphenyl)penteno(1,2-b)pyridine, (5RS,6SR,7SR)-6-carboxy-2-(N-methylisopropylamino)-5-(3,4-methylenedioxyphenyl)-7-(4-methoxphenyl)cyclopenteno(1,2-b)pyridine, (5RS,6SR,7SR)-6-carboxy-2-(N-methylcyclopropylamino)-5-(3,4-methylenedioxyphenyl)-7-(4-methoxphenylcyclopenteno(1,2-b)pyridine, (5RS,6SR,7SR)-2-ethylamino-6-carboxy-7-(2-(2-carboxyethyl-4-methoxyphenyl)-5-(3,4-methylenedioxyphenyl)cyclopenteno(1,2-b)pyridine, (5RS,6SR,7SR)-6-carboxy-7-(2-(2-carboxy-2-propenyl)-4-methoxyphenyl)-2-propylamino-5-(3,4-methylenedioxyphenyl)cyclopenteno(1,2-b)pyridine, (5RS,6SR,7SR)-6-carboxy-7-(2-(2-carboxypropyl)-4-methoxyphenyl)-2-propylamino-5-(3,4-methylenedioxyphenyl)cyclopenteno(1,2-b)pyridine, (5RS,6SR,7SR)-6-carboxy-5-(3,4-methylenedioxyphenyl)-7-(2-(3-methoxypropyl)-4-methoxyphenyl)cyclopenteno(1,2-b)pyridine, (5RS,6SR,7SR)-7-(2-(2-acetoxymethyl-carbonylethyl)-4-methoxyphenyl)-6-carboxy-5-(3,4-methylenedioxyphenyl)cyclopenteno(1,2-b)pyridine, (5RS,6SR,7SR)-6-carboxy-7-(2-(2-hydroxymethylcarbonylethyl)-4-methoxyphenyl)-5-(3,4-methylenedioxyphenyl)cyclopenteno(1,2-b)pyridine, (5RS,6SR,7SR)-6-carboxy-7-(2-(3-carboxypropyl)-4-methoxyphenyl)-5-(3,4-methylenedioxyphenyl)cyclopenteno(1,2-b)pyridine, (5RS,6SR,7SR)-6-carboxy-7-(2-(3-carboxy-2-propylmethyl)-4-methoxyphenyl)-5-(3,4-methylenedioxyphenyl)cyclopenteno(1,2-b)pyridine, (5RS,6SR,7SR)-6-carboxy-7-(2-(2-carboxypropyl)-4-methoxyphenyl)-2-isopropylamino-5-(3,4-methylenedioxyphenyl)cyclopenteno(1,2-b)pyridine, (5RS,6SR,7SR)-6-carboxy-7-(2-(2-carboxy-3-hydroxypropyl)-4-methoxyphenyl)-2-propylamino-5-(3,4-methylenedioxyphenyl)cyclopenteno(1,2-b)pyridine, (5RS,6SR,7SR)-2-ethylamino-6-carboxy-7-(2-(2-carboxypropyl)-4-methoxyphenyl)-5-(3,4-methylenedioxyphenyl)cyclopenteno(1,2-b)pyridine, (5RS,6SR,7SR)-2-isobutylamino-6-carboxy-7-(2-(2-carboxypropyl)-4-methoxyphenyl)-5-(3,4-methylenedioxyphenyl)cyclopenteno(1,2-b)pyridine, (5RS,6SR,7SR)-6-carboxy-7-(2-(2-carboxypropyl)4-methoxyphenyl)-2-cyclopentylamino-5-(3,4-methylenedioxyphenyl)cyclopenteno(1,2-b)pyridine, (5RS,6SR,7SR)-6-carboxy-7-(2-(2-carboxypropyl)-4-methoxyphenyl)-2-(N-(methyl)propylamino)-5-(3,4-methylenedioxyphenyl)cyclopenteno(1,2-b)pyridine, (5RS,6SR,7SR)-5-carboxy-7-(2-(2-carboxypropyl)4-methoxyphenyl)-2-(N-(methyl)isopropylamino-5-(3,4-methylenedioxyphenyl)cyclopenteno(1,2-b)pyridine, (5RS,6SR,7SR )-6-carboxy-7-(2-(2-carboxypropyl)-4-methoxyphenyl)-2-(N-(methyl)ethylamino)-5-(3,4-methylenedioxyphenyl)cyclopenteno(1,2-b)pyridine, (5RS,6SR,7SR)-6-carboxy-7-(2-(2-carboxy-2-hydroxypropyl)-4-methoxyphenyl)-2-(N-(methyl)propylaminol-5-(3,4-methylenedioxyphenyl)cyclopenteno(1,2-b)pyridine, (5RS,6SR,7SR)-6-carboxy-7-(2-(2-carboxyethyl)-4-methoxyphenyl)-2-(N,N-diethylamino)-5-(3,4-methylenedioxyphenyl)cyclopenteno(1,2-b)pyridine, (5RS, 6SR, 7SR)-6-carboxy-7-(2-(2-carboxyethyl)-4-methoxyphenyl)-2-(N-(ethyl)propylamino)-5-(3,4-methylenedioxyphenyl)cyclopenteno(1,2-b)pyridine, (5RS, 6SR, 7SR)-6-carboxy-7-(2-(2-carboxypropyl)-4-methoxyphenyl)-2-(N,N-diethylamino)-5-(3,4-methylenedioxyphenyl)cyclopenteno(1,2-b)pyridine, (5RS, 6SR, 7SR)-6-carboxy-7-(2-(2-carboxypropyl)-4-methoxyphenyl)-2-(N-(ethyl)propylamino)-5-(3,4-methylenedioxyphenyl)cyclopenteno(1,2-b)pyridine, (5RS, 6SR, 7SR)-6-carboxy-7-(2-(2-carboxypropyl)-4-methoxyphenyl)-2-pyrrolidino-5-(3,4-methylenedioxyphenyl)cyclopenteno(1,2-b)pyridine, (5RS,6SR,7SR)-2-(4-hydroxybutylamino)-5-(3,4-methylenedioxyphenyl)-6-ethoxycarbonyl-7-(2-(2-methoxycarbonylpropyl-4-methoxyphenyl)cyclopenteno(1,2-b)pyridine, (5RS,6SR,7SR)-2-Isobutyl-6-carboxy-7-(2-(2-carboxypropyl)-4-methoxyphenyl)-5-(3,4-methylenedioxyphenyl)cyclopenteno(1,2-b)pyridine, (5RS,6SR,7SR)-2-butyl-6-carboxy-7-(2-(2-carboxypropyl)-4-methoxyphenyl)-5-(3,4-methylenedioxyphenyl)cyclopenteno(1,2-b)pyridine, (5RS,6SR,7SR)-6-carboxy-7-(2-(2-carboxypropyl)-4-methoxyphenyl)-2-cyclopentyl-5-(3,4-methylenedioxyphenyl)cyclopenteno(1,-b)pyridine, (5RS,6SR,7SR)-6-carboxy-7-~2-(2-carboxypropyl)-4-methoxyphenyl(-2-(N-(methyl)isopropylamino)-5-(3,4-methylenedioxyphenyl)cyclopenteno(1,2-b)pyridine, (5RS,6SR,7SR)-6-carboxy-7-(2-(2-carboxypropyl)-4-methoxyphenyl)-2-(N-(ethyl)isopropylamino)-5-(3,4-methylenedioxyphenyl)cyclopenteno(1,2-b)pyridine, (5RS,6SR,7SR)-7-(2-(2-carboxypropyl)-4-methoxyphenyl)-5-(3,4-methylenedioxyphenyl)-6-methoxycarbonylcyclopenteno(1,2-b)pyridine, (5RS, 6SR,7SR)-6-carboxy-7-(2-(2-carboxy-3-hydroxypropyl)-4-methoxyphenyl)-2-propylamino-5-(3,4-methylenedioxyphenyl)cyclopenteno(1,2-b)pyridine, (5RS,6SR,7SR)-6-carboxy-7-(2-(2-carboxy-3-hydroxypropyl)-4-methoxyphenyl)-2-(N-(methyl)propylamino)-5-(3,4-methylenedioxyphenyl)cyclopenteno(1,2-b)pyridine, (5RS,6SR,7SR)-6-carboxy-7-(2-(2-carboxy)-4-methoxyphenyl)-2-(N-(methyl)ethylamino-5-(3,4-methylenedioxyphenyl)cyclopenteno(1,2-b)pyridine, (5RS, 6SR,7SR)-2-Secbutylamino-6-carboxy-7-(2-(2-carboxypropyl)-4-methoxyphenyl)-5-(3,4-methylenedioxyphenyl) cyclopenteno(1,2-b)pyridine, (5RS,6SR,7SR)-6-carboxy-7-(2-(3-carboxy-2-methylpropyl)-4-methoxyphenyl)-2-propylamino-5-(3,4-methylenedioxyphenyl)cyclopenteno(1,2-b)pyridine, (5RS,6SR,7SR)-6-tert-butoxycarbonyl-7-(2-(2-methoxyearbonyl-2-propenyl)-4-methoxyphenyl)-5-(3,4-methylenedioxyphenyl)-5-(3,4-methylenedioxyphenyl)cyclopenteno(1,2-b)pyridine, (5RS,6SR,7SR)-2-(1-ethylpropylamino)-6-carboxy-7-(2-(2-carboxypropyl)-4-methoxyphenyl)-5-(3,4-methylenedioxyphenyl)cyclopenteno(1,2-b)pyridine, (5RS,6SR,7SR)-6-carboxy-7-(2-(2-carboxypropyl)-4-methoxyphenyl)-2-tert-butylamino-5-(3,4-methylenedioxyphenyl)cyclopenteno(1,2-b)pyridine, (5RS,6SR,7SR)-6-carboxy-7-(2-(2-carboxy-2-propenyl)-4-methoxyphenyl)-2-isopropylamino-5-(3,4-methylenedioxyphenyl)cyclopenteno(1,2-b)pyridine, (5RS,6SR,7SR)-6-carboxy-7-(2-(2-carboxypropyl)-4-methoxypheny(-1,2-cyclohexylamino-5-(3,4-ethylenedioxyphenyl)cyclopenteno(1,2-b)pyridine, and an isomerically pure compound and a pharmaceutically acceptable salt thereof.

6. The composition of claim 1, wherein the endothelin antagonist is selected from the group consisting of (5RS, 6SR,7SR)-6-carboxy-7-(2-(2-carboxypropyl)-4-methoxyphenyl)-2-butyl-5-(3,4-methylenedioxyphenyl) cyclopenteno(1,2-b)pyridine, and (5RS,6SR,7SR)-2-isopropylamino-6-carboxy-7-(2-(2-carboxypropyl)-4-methoxyphenyl)-5-(3,4-methylenedioxyphenyl) cyclopenteno(1,2-b)pyridine, and isometrically pure compounds thereof.

7. The composition of claim 1, wherein the endothelin antagonist is selected from the group consisting of (5R,6S, 7S)-2-butyl-6-carboxy-7-((R)-2-(2-carboxypropyl)-4-methoxyphenyl)-5-(3,4-methylenedioxyphenyl) cyclopenteno(1,2-b)pyridine, (5R,6S,7S)-2-butyl-6-carboxy-7-((S)-2-(2-carboxypropyl)-4-methoxyphenyl)-5-(3,4-methylenedioxyphenyl)cyclopenteno(1,2-b)pyridine, (5S,6R,7R)-2-butyl -6-carboxy-7-((R)-2-(2-carboxypropyl)-4-methoxyphenyl)-5-(3,4-methylenedioxyphenyl)cyclopenteno(1,2-b)pyridine, (5S, 6R,7R)-2-butyl-6-carboxy-7-((S)-2-(2-carboxypropyl)-4-methoxyphenyl)-5-(3,4-methylenedioxyphenyl) cyclopenteno(1,2-b)pyridine, (5R,6S,7S)-2-isopropylamino-6-carboxy-7-((R)-2-(2-carboxypropyl)-4-methoxyphenyl)-5-(3,4-methylenedioxyphenyl) cyclopenteno(1,2-b)pyridine, (5R,6S,7S)-2-isopropylamino-6-carboxy-7-((S)-2-(2-carboxypropyl)-4-methoxyphenyl)-5-(3,4-methylenedioxyphenyl) cyclopenteno(1,2-b)pyridine, (5S,6R,7R)-2-isopropylamino-6-carboxy-7-((R)-2-(2-carboxypropyl)-4-methoxyphenyl)-5-(3,4-methylenedioxyphenyl) cyclopenteno(1,2-b)pyridine or (5S,6R,7R)-2-isopropylamino-6-carboxy-7-((S)-2-(2-carboxy propyl)-4-methoxyphenyl)-5-(3,4-methylenedioxyphenyl) cyclopenteno(1,2-b)pyridine.

8. The composition of claim 1, wherein the endothelin antagonist is selected from the group consisting of:

(5R,6S,7S)-2-butyl-6-carboxy-7-((R)-2-(2-carboxypropyl)-4-methoxyphenyl)-5-(3,4-methylenedioxyphenyl) cyclopenteno(1,2-b)pyridine, (5R,6S,7S)-2-butyl-6-carboxy-7-((S)-2-(2-carboxypropyl)-4-methoxyphenyl(-5-(3,4-methylenedioxyphenyl) cyclopenteno(1,2-b)pyridine, (5S,6R,7R)-2-butyl-6-carboxy-7-((R)-2-(2-carboxypropyl)-4-methoxyphenyl)-5-(3,4-methylenedioxyphenyl) cyclopenteno(1,2-b)pyridine, and (5S,6R,7R)-2-butyl-6-carboxy-7-((S)-2-(2-carboxypropyl)-4-methoxyphenyl)-5-(3,4-methylenedioxyphenyl) cyclopenteno(1,2-b)pyridine.

9. The composition of claim 1, wherein the endothelin antagonist is an optical isomer.

10. The composition of claim 6, wherein the endothelin antagonist is an optical isomer.

11. The composition of claim 7, wherein the endothelin antagonist is an optical isomer.

12. The composition of claim 8, wherein the endothelin anagonist is an optical isomer.

13. The composition of claim 9, wherein the optical isomer is selected from the group comsisting of:

(5R, 6S, 7S)-2-butyl-6-carboxy-7-((R)-2-(2-carboxypropyl)-4-methoxyphenyl)-5-(3,4-methylenedioxyphenyl) cyclopenteno(1,2-b) pyridine, (5R, 6S, 7S)-2-butyl-6-carboxy-7-((S)-2-(2-carboxypropyl)-4-methoxyphenyl)-5-(3,4-methylenedioxyphenyl) cyclopenteno(1,2-b) pyridine, (5S,6R,7R)-2-butyl-6-carboxy-7-((R)-2-(2-carboxypropyl)-4-methoxyphenyl)-5-(3,4-methylenedioxyphenyl) cyclopenteno (1,2-b)pyridine, and (5S,6R,7R)-2-butyl-6-carboxy-7-((S)-2-(2-carboxypropyl)-4-methoxyphenyl)-5-(3,4-methylenedioxyphenyl) cyctopenteno (1,2-b) pyridine.

14. An optically active compound, which is selected from the group consisting of:

(5R, 6S, 7S)-2-butyl-6-carboxy-7-((R)-2-(2-carboxypropyl)-4-methoxyphenyl)-5-(3,4-methylenedioxyphenyl) cyclopenteno (1,2-b)pyridine, (5R, 6S, 7S)-2-butyl-6-carboxy-7-((S)-2-(2-carboxypropyl)-4-methoxyphenyl)-5-(3,4-methylenedioxyphenyl) cyclopenteno (1,2-b)pyridine, (5S, 6R, 7R)-2-butyl-6-carboxy-7-((R)-2-(2-carboxypropyl)-4-methoxyphenyl)-5-(3,4-methylenedioxyphenyl) cyclopenteno (1,2-b)pyridine, and (5S, 6R, 7R)-2-butyl-6-carboxy-7-((S)-2-(2-carboxypropyl)-4-methoxyphenyl)-5-(3,4-methylenedioxyphenyl) cyclopenteno (1,2-b)pyridine.

15. The optically active compound of claim 14, which is (5R, 6S, 7S)-2-butyl-6-carboxy-7-((R)-2-(2-carboxypropyl)-4-methoxyphenyl)-5-(3,4-methylenedioxyphenyl)cyclopenteno (1,2-b)pyridine.

16. The optically active compound of claim 14, which is (5R, 6S, 7S)-2-butyl-6-carboxy-7-((S)-2-(2-carboxypropyl)-4-methoxyphenyl)-5-(3,4-methylenedioxyphenyl) cyclopenteno (1,2-b)pyridine.

17. The optically active compound of claim 14, which is (5S, 6R, 7R)-2-butyl-6-carboxy-7-((R)-2-(2-carboxypropyl)-4-methoxyphenyl)-5-(3,4-methylenedioxyphenyl)cyclopenteno (1,2-b)pyridine.

18. The optically active compound of claim 14, which is (5S, 6R, 7R)-2-butyl-6-carboxy-7-((S)-2-(2-carboxypropyl)-4-methoxyphenyl)-5-(3,4-methylenedioxyphenyl)cyclopenteno (1,2-b)pyridine.

* * * * *